(12) United States Patent
Cahoon et al.

(10) Patent No.: US 8,497,362 B2
(45) Date of Patent: *Jul. 30, 2013

(54) PLANT DIACYLGLYCEROL ACYLTRANSFERASES

(75) Inventors: Edgar Benjamin Cahoon, Lincoln, NE (US); Anthony J. Kinney, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/975,791

(22) Filed: Dec. 22, 2010

(65) Prior Publication Data

US 2012/0004125 A1 Jan. 5, 2012

Related U.S. Application Data

(60) Division of application No. 12/338,607, filed on Dec. 18, 2008, now abandoned, which is a division of application No. 10/690,994, filed on Oct. 21, 2003, now Pat. No. 7,524,945, which is a continuation of application No. 09/856,018, filed as application No. PCT/US99/28354 on Dec. 1, 1999, now abandoned.

(60) Provisional application No. 60/110,602, filed on Dec. 2, 1998, provisional application No. 60/127,111, filed on Mar. 31, 1999.

(51) Int. Cl.
*C07H 21/04* (2006.01)
*C12N 5/14* (2006.01)
*C12N 15/12* (2006.01)

(52) U.S. Cl.
USPC .......... 536/23.6; 800/278; 800/285; 536/23.2

(58) Field of Classification Search
None
See application file for complete search history.

(56) References Cited

U.S. PATENT DOCUMENTS

| | | | |
|---|---|---|---|
| 6,100,077 A | 8/2000 | Sturley et al. | |
| 6,444,876 B1 | 9/2002 | Lassner et al. | |
| 6,552,250 B1 | 4/2003 | Nykiforuk et al. | |
| 7,524,945 B2 * | 4/2009 | Cahoon et al. | 536/23.6 |

FOREIGN PATENT DOCUMENTS

| | | |
|---|---|---|
| WO | 9745439 | 12/1997 |
| WO | 9963096 | 12/1999 |
| WO | 9967403 | 12/1999 |

OTHER PUBLICATIONS

EMBL Sequence Database Library Accession No: AC0064579, Aug. 1, 1998, Rounsley, S.D. et al., Putative Acyl-COA: Cholesterol Acyltransferase.
Peter Oelkers et al., J. Biol. Chem., vol. 273(41):26765-26771, 1998, Characterization of Two Human Genes Encoding Acyl Coenzyme A: Cholesterol Acyltransferase-related Enzymes.
EMBL Sequence Database Library Accession No: AC005917, X. Lin et al., Nov. 4, 1998, Sequence and analysis of chromosome II of Arabidopsis thaliana.
EMBL Sequence Database Library Accession No: AC003058, S.D. Rounsley et al., Nov. 18, 1997, Sequence and analysis of chromosome II of Arabidopsis thaliana.
Randall J. Weselake et al., J. Exp. Bot., vol. 49(318):33-39, 1998, Triacylglycerol biosynthesis and gene expression in microspore-derived cell suspension cultures of oilseed rape.
Dawn Little et al., Biochem. J., vol. 304:951-958, 1994, Solubilization and characterization of diacylglycerol acyltransferase from microspore-derived cultures of oilseed rape.
Fermin Pacheco-Moises et al., Plant Physiol., vol. 114:1095-1101, 1997, Regulation of Acyltransferase Activity in Immature Maize Embryos by Abscisic Acid and the Osmotic Environment.
Sylvaine Cases et al., Proc. Natl. Acad. Sci., vol. 95:13018-13023, Oct. 1998, Identification of a gene encoding an acyl CoA:diacylglycerol acyltransferase, a key enzyme in triacylglycerol synthesis.
Margrit Frentzen, Fett-Lipid, vol. 100:161-166, 1998, Acyltransferases from basic science to modified seed oils.
Ken'Ichi Ichihara et al., Biochimica et Biophysica Acta, vol. 958:125-129, 1988, Diacylglycerol acyltransferase in maturing safflower seeds: its influences on the fatty acid composition of triacylglycerol.
Cory L. Nykiforuk et al., Plant Physiol., vol. 121(3):1053, 1999, Isolation and characterization of a cDNA encoding s second putative diacylglycerol acyltransferase from a Microspore-Derived cell suspension culture of Brassica napus L. cv Jet Neuf (Accession No. AF164434) (PGR 99-158).
Douglas H. Hobbs et al., FEBS Letters., vol. 452:145-149, 1999, Cloning of a cDNA encoding diacylglycerol actyltransferase from Arabidopsis thaliana and its functional expression.
EMBL Sequence Database Library Accession No: Q9XGR5, Nov. 1, 1999, C.L. Nykiforuk et al., A cDNA exhibiting high homology to diacylglycerol acyltransferase (DGAT) in a microspore-derived cell suspension culture from Brassica napus cv. Jet Neuf.
EMBL Sequence Database Library Accession No: Q9S7F2, May 1, 2000, J. Zou et al., The Arabidopsis thaliana TAG1 gene encodes for a diacylglycerol acyltranferase.
EMBL Sequence Database Library Accession No: AJ238008, Jun. 18, 1999, J. Zou et al., The Arabidopsis thaliana TAG1 gene encodes for a diacylglycerol acyltranferase.
National Center for Biotechnology Information General Identifier No. 3135275, May 16, 1998, Rounsley, S.D. et al., Arabidopsis thaliana chromosome II BAC F27F23 genomic sequence.
National Center for Biotechnology Information General Identifier No. 3135276, May 16, 1998, Rounsley, S.D. et al., Arabidopsis thaliana chromosome II BAC F27F23 genomic sequence.
National Center for Biotechnology Information General Identifier No. 3746533, Oct. 15, 1998, P. Oelkers et al., Characterization of two human genes encoding acyl coenzyme A: cholesterol acyltransferase-related enzymes.
National Center for Biotechnology Information General Identifier No. 3859934, Nov. 11, 1998, S. Cases et al., Identification of a gene encoding an acyl CoA:diacylglycerol acyltransferase, a key enzyme in triacylglycerol synthesis.
National Center for Biotechnology Information General Identifier No. 5050913, Jun. 10, 1999, D. H. Hobbs et al., Cloning of a cDNA encoding diacylglycerol actyltransferase from Arabidopsis thaliana and its functional expression.

(Continued)

*Primary Examiner* — Li Zheng

(57) ABSTRACT

This invention relates to an isolated nucleic acid fragment encoding a diacylglycerol acyltransferase. The invention also relates to the construction of a chimeric gene encoding all or a portion of the diacylglycerol acyltransferase, in sense or antisense orientation, wherein expression of the chimeric gene results in production of altered levels of the diacylglycerol acyltransferase in a transformed host cell.

8 Claims, 3 Drawing Sheets

OTHER PUBLICATIONS

National Center for Biotechnology Information General Identifier No. 5579408, Nov. 30, 1999, C. L. Nykiforuk et al., Isolation and characterization of a cDNA encoding a second putative diacylglycerol acyltransferase from a Microspore-dervied cell suspension culture of Brassica napus L.

Joseph J. Kieber et al., Cell, vol. 72:427-441, 1993, CTR1, a Negative Regulator of the Ethylene Response Pathway in Arabidopsis, Encodes a Member of the Raf Family of Protein Kinases.

National Center for Biotechnology Information General Identifier No. 3135250, May 16, 1998, S. D. Rounsley et al., Arabidopsis thaliana chromosome II BAC F27F23 genomic sequence.

Maria Andersson et al., J. Lipid Res., vol. 35:535-545, 1994, Purification of diacylglycerol:acyltransferase from rat liver to near homogeneity.

Beverly Hay and Jay M. Short, Strategies, vol. 5:16-18, 1992, ExAssist™ Helper Phage and SOLR™ Cells for Lambda ZAP(R) II Excisions.

National Center for Biotechnology Information General Identifier No. 2414087, Sep. 19, 1997, T. Newman et al., Genes galore: a summary of methods for accessing results rom large-scale partial sequencing of anonymous Arabidopsis cDNA clones.

Colette Jako et al., Plant Physiol. vol. 126:861-874, 2001, Seed-Specific Over-Expression of an Arabidopsis cDNA Encoding a Diacylglycerol Acyltransferase Enhances Seed Oil Content and Seed Weight.

Pierrette Bouvier-Nave et al., Eur. J. Biochem. vol. 267:85-96, 2000, Expression in Yeast and Tobacco of Plant cDNAs encoding Acyl CoA:diacylglycerol Acyltransferase.

Vesna Katavic et al., Plant Physiol. vol. 108:399-409, 1995, Alteration of Seed Fatty Acid Composition by an Ethyl Methanesulfonate-Induced Mutation in Arabidopsis thaliana Affecting Diacylglycerol Acyltransferase Activity.

Jitao Zou et al., Plant Journal. vol. 19(6):645-653, 1999, The Arabidopsis thaliana TAG1 mutation in a diacylglycerol acyltransferase gene.

Coleman, R. et al., Triacylglycerol Synthesis in Isolated Fat Cells, The Journal of Biol. Chemistry, vol. 251, No. 15, p. 4537-4543, Aug. 10, 1976.

* cited by examiner

FIGURE 1A

```
SEQ ID NO:25    MG--------------DRGGA-----GSSRRRRTGSRVS-----VQGGSGPKVEEDEVRDAAVS
SEQ ID NO:26    MAILDSAGVTTVTENGGEFVDLDRLRRKSRSDSSNGLLLSGSDNNSPSDDVGAPADVR
SEQ ID NO:02    MAILDSAGVTTVTENGGEFVDLDRLRRKSRSDSSNGLLLSGSDNNSPSDDVGAPADVR
SEQ ID NO:08    ----------------------------------------------------------
SEQ ID NO:14    MVGSDGDG-------DGGGGEAHAGGPRRRAGQ--------LRGRLRDEAAPGSPPRPRPR
SEQ ID NO:16    MAISDEPESVATA------LNHSSLRRRPSATSTAGLFNSPETTDSSGDDLAKDSGSD
SEQ ID NO:22    MSKGNPDPHLP------GSFLPSHGGPPPKPKTPPRTFRNLPSSSTHGPAPSVAAATIAT
                1                                                           60

SEQ ID NO:25    PDLGAGGDAPAPAPAPAHTRDKDGRTSVGDG--------------YW---DLRCHRLQD
SEQ ID NO:26    DRIDSVVNDDAQGTANLAGDNNGGDNNGGDRGGEGRGNADATFTYRPSV-PAHRRARE
SEQ ID NO:02    DRIDSVVNDDAQGTANLAGDNNGGDNNGGDRGGEGRGNADATFTYRPSV-PAHRRARE
SEQ ID NO:08    ----------------------------------------------------------
SEQ ID NO:14    PRPRG----GDSNGRSVLRPGG---------GGGRGGGGDFS-----AFTFRAA-APVHRKAKE
SEQ ID NO:16    DSINS-----DDAAVNSQQQNEK----------QDTDFSVLKFAYRPSV-PAHRKVKE
SEQ ID NO:22    TP-------PSASAAPLPPTVHGEAAH---GAAAAARRD-------ALLPGVGAAHRRVKE
                61                                                          120

SEQ ID NO:25    SLFSSSDSGFSNYR-GILNWCVVMLIILSNARLFLENLIKYGILVDP-IQVVSLFLKDPYSW
SEQ ID NO:26    SPLSSDAIFKQSHAGLFNLCVVVLIAVNSRLIIENLMKYGWLIRTDFWFSSRSLRD---W
SEQ ID NO:02    SPLSSDAIFKQSHAGLFNLCVVVLIAVNSRLIIENLMKYGWLIRTDFWFSSRSLRD---W
SEQ ID NO:08    ----------------------------------------F--NATSLRD---W
SEQ ID NO:14    SPLSSDAIFKQSHAGLFNLCIVVLIAVNSRLIIENLMKYGLLIRAGFWFNDKSLRD---W
SEQ ID NO:16    SPLSSDTIFRQSHAGLFNLCIVVLIAVNSRLIIENLMKYGWLIKSGFWFSSKSLRD---W
SEQ ID NO:22    SPLSSDAIFRQSHAGLLNLCIVVLIAVNSRLIIENLMKYGLLIRAGFWFSARSLGD---W
                121                                                         180
```

FIGURE 1B

```
                    *+  ++         *   **              *+                 *+ +      +++ *  *  + *+
SEQ ID NO:25    PAPCVIIASNIFVVAAFQIEKRLAVGALTEQMGLLLHVVNLATIICFPAAVALLVESITP
SEQ ID NO:26    PLFMCCISLSIFPLAAFTVEKLVLQKYISEPVVIFLHIITMTEVLYPVYVTLRCDSAFL
SEQ ID NO:02    PLFMCWISLSIFPLAAFTVEKLVLQKYISEPVGIFLHIIITMTEVLYPVYVTLRCDSAFL
SEQ ID NO:08    PLLMCCLSLPIFPLGAFAVEKLAFNNLVSDPATTCFHILFTTEIVYPVLVILKCDSAVL
SEQ ID NO:14    PLLMCCLSLPAFPLGAFAVEKLAFNNVITDAVATCLHIFLSTTEIVYPVLVILKCDSAVL
SEQ ID NO:16    PLFMCCLSLVVFPFAAFIVEKLAQRKCIPEPVVVLHIITSTSLFYPVLVILRCDSAFV
SEQ ID NO:22    PLLMCCLITLPIFPLAALMTEKWAQRKLIRDHVSILLHIITTTVLIYPVVVILKCESAVL
                                                                        240

+*       +   +*****+ +++ ++  *    *+    *
SEQ ID NO:25    VGSVFALASYSIMFLKLYSRDVNLWCRQRRVKAKAVSTGKKVSGAAAQQAVSYPDNLTY
SEQ ID NO:26    SGVTLMLLT-CIVWLKLVSYAHTS--YDIRSL----ANAADKANP------EVSYYVSL
SEQ ID NO:02    SGVTLMLLT-CIVWLKLVSYAHTS--YDIRSL----ANAADKANP------EVSYYVSL
SEQ ID NO:08    SGFVLMFIA-CIVWLKLVSFAHTN--HDIGKL----ITSGKKVDNELTAAGIDNLQXPTL
SEQ ID NO:14    SGFLLIFIA-CIVWLKLVSFAHTN--HDIRQL----TMGGKKVDNELSTVDMDNLQPPTL
SEQ ID NO:16    SGVTLMLFS-CVVWLKLVSFAHTN--YDMRAL----TKLVEKGEALLDTLNMDYPYNVSF
SEQ ID NO:22    SGFVLMFIA-SITWLKLVSFAHTN--YDIRIL----SQSIEKGATHGSSIDEENIKGPTI
                                                                        300

**   *****+++++ +*   **++          *   *++++ *+++++++  **
SEQ ID NO:25    RDLYYFIFAPTLCYELN-FPRSPRIRKFLLRRVLEMLFFTQLQVGLIQQWMVPTIQNSM
SEQ ID NO:26    KSLAYFMVAPTLCYQPS-YPRSACIRKGWVARQFAKLVIFTGFMGFIIEQYINPIVRNSK
SEQ ID NO:02    KSLAYFMVAPTLCYQPS-YPRSACIRKGWVARQFAKLVIFTGFMGFIIEQYINPIVRNSK
SEQ ID NO:08    GSLTYFKMAPTLCYQAKVILRTPYVRKGWLVRQVILYLIFTGLQGFIIEQGFIIEQYINPIVVNSQ
SEQ ID NO:14    GNLIYFMMAPTLCYQPS-YPRTSCVRKGWLIRQIILYLIFTGLQGFIIEQYINPIVVNSQ
SEQ ID NO:16    KSLAYFLVAPTLCYQPS-YPRTPYIRKGWLFRQLVKLIIFTGVMGFIIDQYINPIVQNSQ
SEQ ID NO:22    NSVVYFMLAPTLCYQPS-YPRTAFIRKGWVTRQLIKCVVFTGLMGFIIEQYINPIVQNSK
                                                                        360
```

FIGURE 1C

```
                    +*+ +        + + +++*  + +*+*** * +*+** *  *+++* *  ++*++  * *++*+**** ******+
SEQ ID NO:25        KPFKDMDYSRIIERLLKLAVPNHLIWLIFFYWFFHSCLNAVAELLQFGDREFYRDWWNAE
SEQ ID NO:26        HPLKG-DLLYAIERVLKLSVPNLYVWLCMFYCFFHLWLNILAELLCFGDREFYKDWWNAK
SEQ ID NO:02        HPLKG-DLLYAIERVLKLSVPNLYVWLCMFYCFFHLWLNILAELLCFGDREFYKDWWNAK
SEQ ID NO:08        HPLMG-GLLNAVETVLKLSLPNVYLWLCMFYCLFHLWLNILAEILRFGDREFYKDWWNAK
SEQ ID NO:14        HPLKG-GLLNAVETVLKLSLPNVYLWLCMFYAFFHLWLSILAEILRFGDREFYKDWWNAK
SEQ ID NO:16        HPLKG-NLLYATERVLKLSVPNLYVWLCMFYCFFHLWLNILAELLRFGDREFYKDWWNAK
SEQ ID NO:22        HPLNG-NFLDAIERVLKLSVPTLYVWLCMFYSFFHLWLNILAELLRFGDREFYKDWWNAK
                                                        420

+*+ ** ********  ** *+*+*  *   *    +  * ***++  **
SEQ ID NO:25        SVTYFWQNWNIPVHKWCIRHFYKPMLRHGSSKWVARTGVFLTSAFFHEYLVSVPLRMFRL
SEQ ID NO:26        SVGDYWRMWNMPVHKWMPVHKWMVRHIYFPCLRSKIPKTLAIIIAFLVSAVFHELCIAVPCRLFKL
SEQ ID NO:02        SVGDYWRMWNMPVHKWMPVHKWMVRHIYFPCLRSKIPKTLAIIIAFLVSAVFHELCIAVPCRLFKL
SEQ ID NO:08        TIDEYWRKWNMPVHKWIVRHIYFPCMRNGISKEVAVFISFFVSAVLHEYVLLFL-HILKF
SEQ ID NO:14        TIDEYWRKWNMPVHKWIVRHIYFPCMRNGISKEVAVLISFLVSAVLHEICVAVPCRILKF
SEQ ID NO:16        TVEDYWRMWNMPVHKWMIRHLYFPCLRHGLPKAAALLIAFLVSALFHELCIAVPCHIFKL
SEQ ID NO:22        TVEEYWRMWNNMPVHKWIVRHIYFPCIRNGLSKGCAILLAFLVSAVFHELCIAVPCHIFKL
                                                        480

***  +++* * **            +   ++    +      *+++++++*+ + *  * **+++ ++*++*
SEQ ID NO:25        WAFTAMMAQVPLAWIVGRFFQGNYGNAAV-----WVTL-IIGQPVAVLMYVHDYVVLNYDAPVGV
SEQ ID NO:26        WAFLGIMFQVPLIV-FITNYLQERF-GSTVGNMIFWFIFCIFGQPMCVLLYYHD--LMNRKGSMS-
SEQ ID NO:02        WAFLGIMFQVPLIV-FITNYLQERF-GSTVGNMIFWFIFCIFGQPMCVLLYYHD--LMNRKGSMS-
SEQ ID NO:08        WAFLGIMLQIPLI--ILTSYLKNKFSDTMVGNMIFWFFFCIYGQPMCLLLYYHD--VMNR-TEKAK
SEQ ID NO:14        WAFLGIMLQIPLI--VLTAYLKSKFRDTMVGNMIFWFFFCIYGQPMCLLLYYHD--VMNR-IEKAR
SEQ ID NO:16        WAFGGIMFQVPLV--LITNYLQNKFRNSMVGNMIFWFISILGQPMCVLLYYHD--LMNRKGKLD-
SEQ ID NO:22        WAFSGIMFQIPLL--FLTKYLQDKFKNTMVGNMIFWFFFSIVGQPMCVLLYYHD--VMNRQAQTNG
                                                                                        545
```

PLANT DIACYLGLYCEROL ACYLTRANSFERASES

This application is a divisional of U.S. application Ser. No. 12/338,607, filed Dec. 18, 2008, now abandoned, which is a divisional of U.S. application Ser. No. 10/690,994, filed Oct. 21, 2003, now U.S. Pat. No. 7,524,945, issued Apr. 28, 2009, which is a continuation of U.S. application Ser. No. 09/856,018, filed May. 16, 2001, now abandoned, which is a National Stage Application of PCT/US99/28354, filed Dec. 1, 1999, now expired, which claims the benefit of U.S. Provisional Application No. 60/110602, filed Dec. 2, 1998 now expired, and U.S. Provisional Application No. 60/127111, filed Mar. 31, 1999 now expired.

FIELD OF THE INVENTION

This invention is in the field of plant molecular biology. More specifically, this invention pertains to nucleic acid fragments encoding diacylglycerol acyltransferase in plants and seeds.

BACKGROUND OF THE INVENTION

In eukaryotic cells triacylglycerols are quantitatively the most important storage form of energy. Acyl CoA:diacylglycerol acyltransferase (DGAT, EC 2.3.1.20) uses fatty acyl CoA and diacylglycerol as substrates to catalyze the only committed step in triacylglycerol synthesis. DGAT plays a fundamental role in the metabolism of cellular glycerolipids. Because it is an integral membrane protein, DGAT has yet to be purified to homogeneity. A mouse cDNA encoding a protein with DGAT activity has been isolated by using a sequence tag clone sharing regions of similarity with an acyl CoA cholesterol acyltransferase. This mouse DGAT has been cloned, sequenced and expressed in insect cells and its activity characterized (Cases, S. et al. (1998) *Proc. Natl. Acad. Sci. USA* 95:13018-13023).

DGAT is important for the generation of seed oils, thus overexpression of DGAT may be useful for increasing oil content of oilseeds and suppression of DGAT may result in the diversion of carbon into other metabolites.

SUMMARY OF THE INVENTION

The present invention relates to a composition comprising an isolated polynucleotide or polypeptide of the present invention.

The present invention relates to an isolated polynucleotide of the present invention comprising the nucleotide sequence comprising at least one of 30 contiguous nucleotides of a nucleic acid sequence selected from the group consisting of SEQ ID NOs:1, 3, 5, 7, 9, 11, 13, 15, 17, 19 and 21.

The present invention relates to an expression cassette comprising an isolated polynucleotide of the present invention operably linked to a promoter.

The present invention relates to an isolated polynucleotide comprising a nucleotide sequence encoding a first polypeptide of at least 50 amino acids that has at least 60% identity based on the Clustal method of alignment when compared to a polypeptide selected from the group consisting of SEQ ID NOs:4, 6, 8, 10, 14, 20 and 22 or an isolated polynucleotide comprising the complement of the nucleotide sequence.

The present invention relates to an isolated polynucleotide comprising a nucleotide sequence encoding a first polypeptide of at least 50 amino acids that has at least 85% identity based on the Clustal method of alignment when compared to a polypeptide selected from the group consisting of SEQ ID NOs:18 and 20.

It is preferred that the isolated polynucleotide of the claimed invention consists of a nucleic acid sequence selected from the group consisting of SEQ ID NOs:1, 3, 5, 7, 9, 11, 13, 15, 17, 19 and 21 that codes for the polypeptide selected from the group consisting of SEQ ID NOs:2, 6, 8, 10, 14, 16, and 22. The present invention also relates to an isolated polynucleotide comprising a nucleotide sequences of at least one of 40 (preferably at least one of 30) contiguous nucleotides derived from a nucleotide sequence selected from the group consisting of SEQ ID NOs:1, 3, 5, 7, 9, 11, 13, 15, 17, 19, 21, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a polypeptide of at least 50 amino acids that has at least 60% identity based on the Clustal method of alignment when compared to a polypeptide selected from the group consisting of a diacylglycerol acyltransferase polypeptide of SEQ ID NOs:4, 6, 8, 10, 14, 20 and 22.

The present invention relates to a polypeptide of at least 50 amino acids that has at least 85% identity based on the Clustal method of alignment when compared to a polypeptide selected from the group consisting of SEQ ID NOs:18 and 20.

The present invention relates to a polypeptide of at least 50 amino acids that has at least 80% identity based on the Clustal method of alignment when compared to a polypeptide of SEQ ID NO:2.

The present invention relates to a method of selecting an isolated polynucleotide that affects the level of expression of a diacylglycerol acyltransferase polypeptide in a host cell, preferably a plant cell, the method comprising the steps of:
 constructing an isolated polynucleotide of the present invention or an isolated chimeric gene of the present invention;
 introducing the isolated polynucleotide or the isolated chimeric gene into a host cell;
 measuring the level a diacylglycerol acyltransferase polypeptide in the host cell containing the isolated polynucleotide; and
 comparing the level of a diacylglycerol acyltransferase polypeptide in the host cell containing the isolated polynucleotide with the level of a diacylglycerol acyltransferase polypeptide in a host cell that does not contain the isolated polynucleotide.

The present invention relates to a method of obtaining a nucleic acid fragment encoding a substantial portion of a diacylglycerol acyltransferase polypeptide gene, preferably a plant diacylglycerol acyltransferase polypeptide gene, comprising the steps of: synthesizing an oligonucleotide primer comprising a nucleotide sequence of at least one of 40 (preferably at least one of 30) contiguous nucleotides derived from a nucleotide sequence selected from the group consisting of SEQ ID NOs:1, 3, 5, 7, 9, 11, 13, 15, 17, 19, 21, and the complement of such nucleotide sequences; and amplifying a nucleic acid fragment (preferably a cDNA inserted in a cloning vector) using the oligonucleotide primer. The amplified nucleic acid fragment preferably will encode a portion of a diacylglycerol acyltransferase amino acid sequence.

The present invention also relates to a method of obtaining a nucleic acid fragment encoding all or a substantial portion of the amino acid sequence encoding a diacylglycerol acyltransferase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a diacylglycerol acyltransferase, the method comprising the steps of: (a) transforming a host cell with a chimeric gene comprising a nucleic acid fragment encoding a diacylglycerol acyltransferase, operably linked to suitable regulatory sequences; (b) growing the transformed host cell under conditions that are suitable for expression of the chimeric gene wherein expression of the chimeric gene results in production of diacylglycerol acyltransferase in the transformed host cell; (c) optionally purifying the diacylglycerol acyltransferase expressed by the transformed host cell; (d) treating the diacylglycerol acyltransferase with a compound to be tested; and (e) comparing the activity of the diacylglycerol acyltransferase that has been treated with a test compound to the activity of an untreated diacylglycerol acyltransferase, thereby selecting compounds with potential for inhibitory activity.

BRIEF DESCRIPTION OF THE DRAWING AND SEQUENCE DESCRIPTIONS

The invention can be more fully understood from the following detailed description and the accompanying drawing and Sequence Listing which form a part of this application.

FIGS. 1A, 1B, and 1C show an alignment of the amino acid sequences from *Mus musculus* diacylglycerol acetyltransferase (SEQ ID NO:25), the instant *Arabidopsis thaliana* diacylglycerol acetyltransferase (araebcF; SEQ ID NO:2), the instant corn diacylglycerol acetyltransferase (cpj1c.pk005.h23; SEQ ID NO:8), the instant rice diacylglycerol acetyltransferase (rls24.pk0034.d8:fis; SEQ ID NO:14), the instant soybean diacylglycerol acetyltransferase (sr1.pk0098.a8; SEQ ID NO:16), and the instant wheat diacylglycerol acetyltransferase (wr1.pk0119.b6:fis; SEQ ID NO:22). Amino acids which are identical among all sequences are indicated with an asterisk (*) above the alignment while those conserved only among the plant sequences are indicated by a plus sign (+). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Diacylglycerol Acyltransferases

| Protein | Clone Designation | SEQ ID NO: (Nucleotide) | SEQ ID NO: (Amino Acid) |
|---|---|---|---|
| *Arabidopsis* Diacylglycerol Acyltransferase | araebcF | 1 | 2 |
| Corn Diacylglycerol Acyltransferase | Contig of: cpj1c.pk005.h23 cen3n.pk0010.c10 ccol.pk0029.b6 | 3 | 4 |
| Corn Diacylglycerol Acyltransferase | cen3n.pk0113.e12 | 5 | 6 |
| Corn Diacylglycerol Acyltransferase | cpj1c.pk005.h23 | 7 | 8 |
| Corn Diacylglycerol Acyltransferase | Contig of: p0042.cspaf49r p0122.ckamb57r p0125.czaau61rb | 9 | 10 |
| Rice Diacylglycerol Acyltransferase | rls24.pk0034.d8 | 11 | 12 |
| Rice Diacylglycerol Acyltransferase | rls24.pk0034.d8:fis | 13 | 14 |
| Soybean Diacylglycerol Acyltransferase | sr1.pk0098.a8 | 15 | 16 |
| Soybean Diacylglycerol Acyltransferase | src3c.pk013.h18 | 17 | 18 |
| Wheat Diacylglycerol Acyltransferase | wr1.pk0119.b6 | 19 | 20 |
| Wheat Diacylglycerol Acyltransferase | wr1.pk0119.b6:fis | 21 | 22 |

The nucleotide sequences having SEQ ID NOs:3, 11, 17, and 19 and the amino acid sequences having SEQ ID NOs:4, 12, 18, and 20 were presented in the U.S. Provisional Application No. 60/110,602, filed Dec. 2, 1998. The nucleotide sequences having SEQ ID NOs:1 and 15 as well as the amino acid sequences having SEQ ID NOs:2 and 16 were added in the U.S. Provisional Application No. 60/127,111, filed Mar. 3, 1999. The nucleotide sequence presented in SEQ ID NO:15 encodes an entire soybean diacylglycerol acyltransferase whose amino acid sequence is presented in SEQ ID NO:16, the amino acid sequence presented in SEQ ID NO:17 encodes only a portion of the enzyme. The nucleotide sequence presented in SEQ ID NO:7 corresponds to the full insert sequence and encodes a protein identical to that of SEQ ID NO:4. The nucleotide sequences presented in SEQ ID NOs:11 and 19 correspond to a portion of those presented in SEQ ID NOs:13 and 21.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least one of 40 contiguous nucleotides, preferably at least one of 30 contiguous nucleotides, most preferably one of at least 15 contiguous nucleotides, of the nucleic acid sequence of the SEQ ID NOs:1, 3, 5, 7, 9, 11, 13, 15, 17, 19, 21, and the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-á-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs: 1, 5, 7, 9, 13, 15, 21, and the complement of such nucleotide sequences may be used in methods of selecting an isolated polynucleotide that affects the expression of a polypeptide in a plant cell. A method of selecting an isolated polynucleotide that affects the level of expression of a polypeptide such as diacylglyercol acyltransferase, in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several diacylglycerol acyltransferases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other diacylglycerol acyltransferases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as diacylglycerol acyltransferases) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the oil content in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the chimeric gene described above may be further supplemented by altering the coding sequence to encode the instant polypeptide with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptide (or portions thereof) may be produced in heterologous host cells, particularly in the cells of microbial hosts, and can be used to prepare antibodies to the these proteins by methods well known to those skilled in the art. The antibodies are useful for detecting the polypeptide of the instant invention in situ in cells or in vitro in cell extracts. Preferred heterologous host cells for production of the instant polypeptide are microbial hosts. Microbial expression systems and expression vectors containing regulatory sequences that direct high level expression of foreign proteins are well known to those skilled in the art. Any of these could be used to construct a chimeric gene for production of the instant polypeptide. This chimeric gene could then be introduced into appropriate microorganisms via transformation to provide high level expression of the encoded diacylglycerol acyltransferase. An example of a vector for high level expression of the instant polypeptide in a bacterial host is provided (Example 7).

Additionally, the instant polypeptide can be used as a target to facilitate design and/or identification of inhibitors of those enzymes that may be useful as herbicides. This is desirable because the diacylglycerol acyltransferase described herein catalyzes the committed step in triacylglycerol biosynthesis. Accordingly, inhibition of the activity of the enzyme described herein could lead to inhibition plant growth. Thus, the instant diacylglycerol acyltransferase could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide, Academic press* 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402-9406; Koes et al. (1995) *Proc. Natl. Acad. Sci. USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various *Arabidopsis*, corn, rice, soybean, and wheat tissues were prepared. The characteristics of the libraries are described below.

er's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding diacylglycerol acyltransferases were identified by conducting BLAST (Basic Local Alignment Search Tool; Altschul et al. (1993) J. Mol. Biol. 215: 403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared

TABLE 2 cDNA Libraries from *Arabidopsis*, Corn, Rice, Soybean, and Wheat

| Library | Tissue | Clone |
|---------|--------|-------|
| ara | 3 day-old *Arabidopsis thaliana* seedling hypocotyls | araebcF |
| cco1 | Corn Cob of 67 Day Old Plants Grown in Green House | cco1.pk0029.b6 |
| cen3n | Corn Endosperm 20 Days After Pollination* | cen3n.pk0010.c10 cen3n.pk0113.e12 |
| cpj1c | Corn Pooled BMS Treated With Chemicals Related to Membrane Ionic Force** | cpj1c.pk005.h23 |
| p0042 | Corn Seedling After 10 Day Drought Stress Heat Shocked for 24 Hours at 45° C. | p0042.cspaf49r |
| p0122 | Corn Pith Tissue from Internode Subtending Ear Node 5 Days After Pollination* | p0122.ckamb57r |
| p0125 | Corn Anther Prophase I* | p0125.czaau61rb |
| rls24 | Rice Leaf 15 Days After Germination, 24 Hours After Infection of Strain *Magaporthe grisea* 4360-R-67 (AVR2-YAMO); Susceptible | rls24.pk0034.d8 |
| sr1 | Soybean Root | sr1.pk0098.a8 |
| src3c | Soybean 8 Day Old Root Infected With Cyst Nematode | src3c.pk013.h18 |
| wr1 | Wheat Root From 7 Day Old Seedling | wr1.pk0119.b6 |

*These libraries were normalized essentially as described in U.S. Pat. No. 5,482,845, \incorporated herein by reference.
**Chemicals used included valinomycin, bafilomycin A1, oligomycin, and ionomycin.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturfor similarity to all publicly available protein sequences contained in the "nr" database using the BLASTX algorithm (Gish and States (1993) Nat. Genet. 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of Corn, Rice, and Wheat cDNA Clones Encoding Diacylglycerol Acyltransferase The BLASTX search using the EST sequences from clones listed in Table 3 revealed similarity of the proteins encoded by the cDNAs to a putative Acyl CoA cholesterol acyltransferase related gene product from *Arabidopsis thaliana* (NCBI General Identifier No. 3135276), and to diacylglycerol acyltransferases from *Homo sapiens* and *Mus musculus* (NCBI General Identifier Nos. 3746533, and 3859934, respectively). Animal acyl CoA cholesterol acyltransferases have recently been shown to be related to diacylglycerol acyltransferases (Cases et al. (1998) *Proc. Natl. Acad. Sci. USA* 95:13018-13023). The sequences included here are therefore more likely to be diacylglycerol acyltransferases than acyl CoA cholesterol acyltransferases since cholesterol is only a very minor constituent of plant sterols. Shown in Table 3 are the BLAST results for individual ESTs ("EST"), or contigs assembled from two or more ESTs ("Contig"):

TABLE 3

BLAST Results for Clones Encoding Polypeptides Homologous to Diacylglycerol Acyltransferase

| | | BLAST pLog Score | |
|---|---|---|---|
| Clone | Status | 3746533 | 3859934 |
| Contig of: cpj1c.pk005.h23 cen3n.pk0010.c10 cco1.pk0029.b6 | Contig | 59.70 | 59.52 |
| cen3n.pk0113.e12 | EST | 38.00 | 39.00 |
| rls24.pk0034.d8 | EST | 3.70 | 3.70 |
| wr1.pk0119.b6 | EST | 4.52 | 4.40 |

The BLASTX search using the EST sequences from clones listed in Table 4 revealed similarity of the proteins encoded by the cDNAs to putative diacylglycerol acyltransferases from *Arabidopsis thaliana* and *Brassica napus* (NCBI General Identifier Nos. 5050913 and 5579408, respectively). Shown in Table 4 are the BLAST results for the sequences of the entire cDNA inserts comprising the indicated cDNA clones ("FIS"), contigs assembled from two or more ESTs ("Contig"), or sequences encoding the entire protein derived from an FIS and PCR ("CGS"):

TABLE 4

BLAST Results for Clones Encoding Polypeptides Homologous to Diacylglycerol, Acyltransferase

| | | BLAST pLog Score | |
|---|---|---|---|
| Clone | Status | 5050913 | 5579408 |
| cpj1c.pk005.h23 | FIS | 113.00 | 116.00 |
| Contig of: p0042.cspaf49r p0122.ckamb57r p0125.czaau61rb | Contig | 111.00 | 109.00 |
| rls24.pk0034.d8:fis | CGS | >250.00 | 173.00 |
| wr1.pk0119.b6:fis | CGS | 177.00 | 173.00 |

Sequence alignments (see Example 4) and BLAST scores and probabilities indicate that the nucleic acid fragments comprising the instant cDNA clones encode a substantial portion of a corn diacylglycerol acyltransferase and entire corn, rice, and wheat diacylglycerol acyltransferases. These sequences represent the first corn, rice, and wheat sequences encoding diacylglycerol acyltransferases.

Example 4

Cloning and Sequencing of cDNAs Encoding Entire Soybean and *Arabidopsis thaliana* Diacylglycerol Acyltransferases The BLASTX search using the EST sequences from clones listed in Table 5 revealed similarity of the proteins encoded by the cDNAs to a hypothetical protein from *Arabisopsis thaliana* and the *Mus musculus* DGAT (NCBI General Identifier Nos: 3135275 and 3859934, respectively). The sequence of the entire cDNA insert in clone src3c.pk013.h18 was determined, it was found to contain insertions and deletions with respect to known diacylglycerol acetyltransferases. Clone srl.pk0098.a8 was found by searching the DuPont EST database for soybean sequences with similarities to the entire cDNA sequence from clone src3c.pk013.h18.

Because it was suspected that the *Arabidopsis thaliana* putative ACAT sequence encoded only the C-terminal half of a DGAT, an *Arabidopsis thaliana* DGAT sequence was obtained by PCR from a public library described by Kieber et al. (1993) *Cell* 72:427-441. This library was prepared from polyA+ RNA isolated from 3 day-old *Arabidopsis thaliana* (Columbia) seedling hypocotyls and consisted of 2 to 3 kb size-selected cDNA inserts cloned into the EcoRI site of lambda-ZAPII (Stratagene). Prior to use in PCR reactions, the library was converted into plasmid form by mass-excision following Hay and Short (1992) *Strategies* 5:16-18) to yield pBluescript SK(-)-containing cDNA inserts. Primers used for PCR were:

AtDGx5'
5' CTT AGC TTC TTC CTT CAA TC 3'

AT-DGAT3'
5' TTT CTA GAC TCG AGT GAA CAG TTG TTT CAT GAC 3'

The PCR primers were designed based on EST and genomic sequences in the public domain. An *Arabidopsis thaliana* EST sequence (GenBank General Identifier No. 2414087) was used to design the 3' primer (AT-DGAT3; SEQ ID NO:23). The 5' primer (AtDGx5; SEQ ID NO:24) was based on *Arabidopsis* genomic sequence information found in NCBI General Identifier No. 3135250, but could not have been readily predicted as the appropriate 5' end of the cDNA, based on public sequences. The 5' primer was designed to be located upstream of a stop codon located in the same reading frame as the codon for the putative start methionine. The PCR product from this primer is therefore likely to contain the entire cDNA.

Shown in Table 5 are the BLAST results for individual ESTs ("EST"), or sequences encoding the entire protein derived from an FIS and PCR ("CGS"):

TABLE 5

BLAST Results for Sequences Encoding Polypeptides Homologous to Diacylglycerol Acyltransferase

| | | BLAST pLog Score | |
|---|---|---|---|
| Clone | Status | 3135275 | 3859934 |
| araebcF | CGS | 132.00 | 77.70 |
| src3c.pk013.h18 | EST | 3.00 | |
| srl.pk0098.a8 | CGS | 105.00 | 81.52 |

FIGS. 1A, 1B, and 1C present an alignment of the amino acid sequences set forth in SEQ ID NOs:2, 8, 14, 16, and 22 and the *Mus musculus* and *Arabidopsis thaliana* diacylglycerol acetyltransferase sequences (SEQ ID NO:25 and SEQ ID NO:26). The data in Table 6 represents a calculation of the percent identity of the amino acid sequences set forth in SEQ ID NOs:2, 8, 14, 16, and 22 and the *Mus musculus* and *Arabidopsis thaliana* diacylglycerol acetyltransferase sequences (SEQ ID NO:25 and SEQ ID NO:26).

TABLE 6

Percent Identity of Amino Acid Sequences Deduced From the Nucleotide Sequences of cDNA Clones Encoding Polypeptides Homologous to Diacylglycerol Acyltransferase

| | Percent Identity to | |
|---|---|---|
| SEQ ID NO. | 3859934 | 5050913 |
| 2 | 31.9 | 99.6 |
| 8 | 31.5 | 56.0 |
| 14 | 29.3 | 57.4 |
| 16 | 30.9 | 65.9 |
| 22 | 29.9 | 58.7 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of three corn, one entire *Arabidopsis*, one entire rice, and one entire wheat diacylglycerol acyltransferase. These sequences represent the first *Arabidopsis*, corn, rice, soybean, and wheat sequences encoding diacylglycerol acyltransferase.

Example 5

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 6

Expression of Chimeric Genes in Dicot Cells

A seed-specific expression cassette composed of the promoter and transcription terminator from the gene encoding the 0 subunit of the seed storage protein phaseolin from the bean *Phaseolus vulgaris* (Doyle et al. (1986) *J. Biol. Chem.* 261:9228-9238) can be used for expression of the instant polypeptide in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptide can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Diacylglycerol Acyltransferases The polypeptide described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptide may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptide, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptide are expressed as fusion proteins, the purification protocol may include the use of an affinity resin which is specific for the fusion protein tag attached to the expressed enzyme or an affinity resin containing ligands which are specific for the enzyme. For example, the instant polypeptide may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptide disclosed herein. Assays may be conducted under well known experimental conditions which permit optimal enzymatic activity. For example, assays for diacylglycerol acyltransferases are presented by M. Andersson et al. ((1994) *J. Lipid Res.* 35:535-545).

What is claimed is:

1. A method of selecting an isolated polynucleotide that affects the level of expression of a diacylglycerol acyltransferase polypeptide in a plant cell, the method comprising the steps of:
   (a) constructing a recombinant DNA construct comprising a promoter operably linked to an isolated polynucleotide comprising a nucleotide sequence of at least 30 contiguous nucleotides of SEQ ID NO:15;
   (b) introducing the recombinant DNA construct into a plant cell;
   (c) measuring the level of diacylglycerol acyltransferase polypeptide in the plant cell containing the recombinant DNA construct;
   (d) comparing the level of diacylglycerol acyltransferase polypeptide in the plant cell containing the recombinant DNA construct with the level of diacylglycerol acyltransferase polypeptide in a plant cell that does not contain the isolated polynucleotide; and
   (e) selecting for the isolated polynucleotide that affects the level of expression of the diacylglycerol acyltransferase polypeptide in the plant cell.

2. The method of claim 1, wherein the isolated polynucleotide comprises at least 60 contiguous nucleotides of SEQ ID NO:15.

3. The method of claim 1, wherein the isolated polynucleotide comprises a fragment of SEQ ID NO:15 encoding at least 50 amino acid residues of SEQ ID NO:16.

4. The method of claim 1, wherein the isolated polynucleotide comprises a fragment of SEQ ID NO:15 encoding at least 100 amino acid residues of SEQ ID NO:16.

5. A method of selecting an isolated polynucleotide that affects the level of expression of a diacylglycerol acyltransferase polypeptide in a plant, the method comprising the steps of:
   (a) constructing a recombinant DNA construct comprising a promoter operably linked to an isolated nucleotide sequence of at least 30 contiguous nucleotides of SEQ ID NO:15;
   (b) transforming a plant cell with the recombinant DNA construct of (a);
   (c) regenerating a transgenic plant from the transformed plant cell of (b), wherein the transgenic plant comprises the recombinant DNA construct;
   (d) measuring the level of diacylglycerol acyltransferase polypeptide in the transgenic plant comprising the recombinant DNA construct;
   (e) comparing the level of diacylglycerol acyltransferase polypeptide in the transgenic plant comprising the recombinant DNA construct with the level of diacylglycerol acyltransferase polypeptide in a plant that does not comprise the recombinant DNA construct; and
   (f) selecting for the isolated polynucleotide that affects the level of expression of the diacylglycerol acyltransferase polypeptide in the plant.

6. The method of claim 5, wherein the isolated polynucleotide comprises at least 60 contiguous nucleotides of SEQ ID NO:15.

7. The method of claim 5, wherein the isolated polynucleotide comprises a fragment of SEQ ID NO:15 encoding at least 50 amino acid residues of SEQ ID NO:16.

8. The method of claim 5, wherein the isolated polynucleotide comprises a fragment of SEQ ID NO:15 encoding at least 100 amino acid residues of SEQ ID NO:16.

* * * * *

SEQUENCE LISTING

<160> NUMBER OF SEQ ID NOS: 26

<210> SEQ ID NO 1
<211> LENGTH: 1888
<212> TYPE: DNA
<213> ORGANISM: Arabidopsis thaliana

<400> SEQUENCE: 1
gcttcttcct tcaatccgct ctttccctct ccattagatt ctgtttcctc tttcaatttc    60

-continued

```
ttctgcatgc ttctcgattc tctctgacgc ctcttttctc ccgacgctgt ttcgtcaaac      120
gcttttcgaa atggcgattt tggattctgc tggcgttact acggtgacgg agaacggtgg      180
cggagagttc gtcgatcttg ataggcttcg tcgacggaaa tcgagatcgg attcttctaa      240
cggacttctt ctctctggtt ccgataataa ttctccttcg gatgatgttg gagctcccgc      300
cgacgttagg gatcggattg attccgttgt taacgatgac gctcagggaa cagccaattt      360
ggccggagat aataacggtg gtgcgataa taacggtggt ggaagaggcg gcggagaagg       420
aagaggaaac gccgatgcta cgtttacgta tcgaccgtcg gttccagctc atcggagggc      480
gagagagagt ccacttagct ccgacgcaat cttcaaacag agccatgccg gattattcaa      540
cctctgtgta gtagttctta ttgctgtaaa cagtagactc atcatcgaaa atcttatgaa      600
gtatggttgg ttgatcagaa cggatttctg gtttagttca agatcgctgc gagattggcc      660
gcttttcatg tgttggatat ccctttcgat cttcctttg gctgccttta cggttgagaa       720
attggtactt cagaaataca tatcagaacc tgttggcatc tttcttcata ttattatcac      780
catgacagag gttttgtatc cagtttacgt caccctaagg tgtgattctg ctttttatc       840 aggtgtcact ttgatgctcc tcacttgcat tgtgtggcta agttggttt cttatgctca       900 tactagctat gacataagat ccctagccaa tgcagctgat aaggccaatc ctgaagtctc      960
ctactacgtt agcttgaaga gcttggcata tttcatggtc gctcccacat tgtgttatca     1020
gccaagttat ccacgttctg catgtatacg gaagggttgg gtggctcgtc aatttgcaaa     1080
actggtcata ttcaccggat tcatgggatt tataatagaa caatatataa atcctattgt     1140
caggaactca agcatccttt gaaaggcga tcttctatat gctattgaaa gagtgttgaa      1200
gctttcagtt ccaaatttat atgtgtggct ctgcatgttc tactgcttct tccacctttg     1260
gttaaacata ttggcagagc ttctctgctt cggggatcgt gaattctaca agattggtg      1320 gaatgcaaaa agtgtgggag attactggag aatgtggaat atgcctgttc ataaatggat     1380
ggttcgacat atatacttcc cgtgcttgcg cagcaagata ccaaagacac tcgccattat     1440
cattgctttc ctagtctctg cagtctttca tgagctatgc atcgcagttc cttgtcgtct     1500
cttcaagcta tgggctttc ttgggattat gtttcaggtg cctttggtct tcatcacaaa      1560
ctatctacag gaaaggtttg gctcaacggt ggggaacatg atcttctggt tcatcttctg     1620
cattttcgga caaccgatgt gtgtgcttct ttattaccac gacctgatga accgaaaagg     1680
atcgatgtca tgaaacaact gttcaaaaaa tgactttctt caaacatcta tggcctcgtt     1740
ggatctccgt tgatgttgtg gtggttctga tgctaaaacg acaaatagtg ttataaccat     1800
tgaagaagaa aagaaaatta gagttgttgt atctgcaaaa attttggtag agacacgcaa     1860
acccgtttgg atttttgttat ggagtaaa                                        1888
```

<210> SEQ ID NO 2
<211> LENGTH: 520
<212> TYPE: PRT
<213> ORGANISM: Arabidopsis thaliana

<400> SEQUENCE: 2

```
Met Ala Ile Leu Asp Ser Ala Gly Val Thr Thr Val Thr Glu Asn Gly
 1               5                  10                  15

Gly Gly Glu Phe Val Asp Leu Asp Arg Leu Arg Arg Arg Lys Ser Arg
             20                  25                  30

Ser Asp Ser Ser Asn Gly Leu Leu Leu Ser Gly Ser Asp Asn Asn Ser
         35                  40                  45
```

```
Pro Ser Asp Asp Val Gly Ala Pro Ala Asp Val Arg Asp Arg Ile Asp
    50                  55                  60
Ser Val Val Asn Asp Asp Ala Gln Gly Thr Ala Asn Leu Ala Gly Asp
 65                  70                  75                  80
Asn Asn Gly Gly Gly Asp Asn Asn Gly Gly Arg Gly Gly Gly Gly Glu
                 85                  90                  95
Gly Arg Gly Asn Ala Asp Ala Thr Phe Thr Tyr Arg Pro Ser Val Pro
                100                 105                 110
Ala His Arg Arg Ala Arg Glu Ser Pro Leu Ser Ser Asp Ala Ile Phe
            115                 120                 125
Lys Gln Ser His Ala Gly Leu Phe Asn Leu Cys Val Val Leu Leu Ile
    130                 135                 140
Ala Val Asn Ser Arg Leu Ile Ile Glu Asn Leu Met Lys Tyr Gly Trp
145                 150                 155                 160
Leu Ile Arg Thr Asp Phe Trp Phe Ser Ser Arg Ser Leu Arg Asp Trp
                165                 170                 175
Pro Leu Phe Met Cys Trp Ile Ser Leu Ser Ile Phe Pro Leu Ala Ala
                180                 185                 190
Phe Thr Val Glu Lys Leu Val Leu Gln Lys Tyr Ile Ser Glu Pro Val
            195                 200                 205
Gly Ile Phe Leu His Ile Ile Ile Thr Met Thr Glu Val Leu Tyr Pro
    210                 215                 220
Val Tyr Val Thr Leu Arg Cys Asp Ser Ala Phe Leu Ser Gly Val Thr
225                 230                 235                 240
Leu Met Leu Leu Thr Cys Ile Val Trp Leu Lys Leu Val Ser Tyr Ala
                245                 250                 255
His Thr Ser Tyr Asp Ile Arg Ser Leu Ala Asn Ala Ala Asp Lys Ala
                260                 265                 270
Asn Pro Glu Val Ser Tyr Tyr Val Ser Leu Lys Ser Leu Ala Tyr Phe
            275                 280                 285
Met Val Ala Pro Thr Leu Cys Tyr Gln Pro Ser Tyr Pro Arg Ser Ala
    290                 295                 300
Cys Ile Arg Lys Gly Trp Val Ala Arg Gln Phe Ala Lys Leu Val Ile
305                 310                 315                 320
Phe Thr Gly Phe Met Gly Phe Ile Ile Glu Gln Tyr Ile Asn Pro Ile
                325                 330                 335
Val Arg Asn Ser Lys His Pro Leu Lys Gly Asp Leu Leu Tyr Ala Ile
                340                 345                 350
Glu Arg Val Leu Lys Leu Ser Val Pro Asn Leu Tyr Val Trp Leu Cys
            355                 360                 365
Met Phe Tyr Cys Phe Phe His Leu Trp Leu Asn Ile Leu Ala Glu Leu
    370                 375                 380
Leu Cys Phe Gly Asp Arg Glu Phe Tyr Lys Asp Trp Trp Asn Ala Lys
385                 390                 395                 400
Ser Val Gly Asp Tyr Trp Arg Met Trp Asn Met Pro Val His Lys Trp
                405                 410                 415
Met Val Arg His Ile Tyr Phe Pro Cys Leu Arg Ser Lys Ile Pro Lys
                420                 425                 430
Thr Leu Ala Ile Ile Ile Ala Phe Leu Val Ser Ala Val Phe His Glu
            435                 440                 445
Leu Cys Ile Ala Val Pro Cys Arg Leu Phe Lys Leu Trp Ala Phe Leu
    450                 455                 460
Gly Ile Met Phe Gln Val Pro Leu Val Phe Ile Thr Asn Tyr Leu Gln
465                 470                 475                 480
```

```
Glu Arg Phe Gly Ser Thr Val Gly Asn Met Ile Phe Trp Phe Ile Phe
            485                 490                 495

Cys Ile Phe Gly Gln Pro Met Cys Val Leu Leu Tyr Tyr His Asp Leu
        500                 505                 510

Met Asn Arg Lys Gly Ser Met Ser
        515                 520

<210> SEQ ID NO 3
<211> LENGTH: 1281
<212> TYPE: DNA
<213> ORGANISM: Zea mays
<220> FEATURE:
<221> NAME/KEY: unsure
<222> LOCATION: (356)
<223> OTHER INFORMATION: n = a, c, g, or t
<220> FEATURE:
<221> NAME/KEY: unsure
<222> LOCATION: (427)
<223> OTHER INFORMATION: n = a, c, g, or t
<220> FEATURE:
<221> NAME/KEY: unsure
<222> LOCATION: (1188)
<223> OTHER INFORMATION: n = a, c, g, or t
<220> FEATURE:
<221> NAME/KEY: unsure
<222> LOCATION: (1196)
<223> OTHER INFORMATION: n = a, c, g, or t
<220> FEATURE:
<221> NAME/KEY: unsure
<222> LOCATION: (1198)
<223> OTHER INFORMATION: n = a, c, g, or t
<220> FEATURE:
<221> NAME/KEY: unsure
<222> LOCATION: (1236)
<223> OTHER INFORMATION: n = a, c, g, or t
<220> FEATURE:
<221> NAME/KEY: unsure
<222> LOCATION: (1242)
<223> OTHER INFORMATION: n = a, c, g, or t
<220> FEATURE:
<221> NAME/KEY: unsure
<222> LOCATION: (1244)
<223> OTHER INFORMATION: n = a, c, g, or t
<220> FEATURE:
<221> NAME/KEY: unsure
<222> LOCATION: (1248)
<223> OTHER INFORMATION: n = a, c, g, or t
<220> FEATURE:
<221> NAME/KEY: unsure
<222> LOCATION: (1259)
<223> OTHER INFORMATION: n = a, c, g, or t
<220> FEATURE:
<221> NAME/KEY: unsure
<222> LOCATION: (1266)
<223> OTHER INFORMATION: n = a, c, g, or t
<220> FEATURE:
<221> NAME/KEY: unsure
<222> LOCATION: (1280)
<223> OTHER INFORMATION: n = a, c, g, or t

<400> SEQUENCE: 3
tttaatgcta catcattgcg agactggcca ctgctaatgt gttgccttag tctacccata      60
tttccccttg gtgcatttgc agtcgaaaag ttggcattca acaatctcgt tagtgatcct     120
gctactacct gttttcacat ccttttaca acatttgaaa ttgtatatcc agtgctcgtg     180
attcttaagt gtgattctgc agtttttatca ggctttgtgt tgatgtttat tgcctgcatt     240
gtttggctga agcttgtatc ttttgcacat acaaaccatg atataaggaa aactgatcac     300
aagcggcaag aaggttgata atgaactgac cgcggctggc atagataatt tacaanctcc     360
aactcttggg agtctaacat acttcaagat ggctccgaca ctctgttatc aagccaaagt     420
```

```
tatcctncga acaccttatg ttagaaaagg ttggctggtc cgtcaagtta ttctatactt    480
gatatttact ggtctccaag gattcattat tgagcaatac ataaatccta ttgttgtgaa    540
ctctcaacat ccattgatgg gaggattact gaatgctgta gagactgttt tgaagctctc    600
attaccaaat gtctacctgt ggctttgcat gttttattgc cttttccatc tgtggttaaa    660
catacttgct gagattcttc gatttggtga ccgagaattc tacaaagact ggtggaatgc    720
aaagacaatt gatgagtact ggagaaaatg aacatgcct gtgcataaat ggattgttcg      780
tcatatatat ttcccttgca tgcgaaatgg tatatcaaag gaagttgctg ttttatatc      840 gttctttgtt tctgctgtac ttcatgagtt atgtgttgct gttccctgcc acatactcaa    900
gttctgggct tccttaggaa tcatgcttca gattcccctc atcatattga catcatacct    960
caaaaataaa ttcagtgaca caatggttgg caatatgatc ttttggtttt ttttctgcat    1020
atacgggcag ccaatgtgtg ttctattgta ttaccatgat gtgatgaacc ggactgagaa    1080
ggcaaaataa ccatcgtgtag atcttttgg gtttcatttc tccatcatgg aaactgaaac     1140
ataactgtgc acacataaac agcatcgtgt ctcaattttt taaaaaanaa aagaananca    1200 caaaaaccc aggggggccg gtaccaatcc ccaaantatc gntnaccncc cacggcgtnt      1260
taaacncgta cggaaaaccn g                                               1281
```

<210> SEQ ID NO 4
<211> LENGTH: 361
<212> TYPE: PRT
<213> ORGANISM: Zea mays
<220> FEATURE:
<221> NAME/KEY: UNSURE
<222> LOCATION: (119)
<223> OTHER INFORMATION: Xaa = ANY AMINO ACID

<400> SEQUENCE: 4

Phe Asn Ala Thr Ser Leu Arg Asp Trp Pro Leu Leu Met Cys Cys Leu
  1               5                  10                  15

Ser Leu Pro Ile Phe Pro Leu Gly Ala Phe Ala Val Glu Lys Leu Ala
             20                  25                  30

Phe Asn Asn Leu Val Ser Asp Pro Ala Thr Thr Cys Phe His Ile Leu
         35                  40                  45

Phe Thr Thr Phe Glu Ile Val Tyr Pro Val Leu Val Ile Leu Lys Cys
     50                  55                  60

Asp Ser Ala Val Leu Ser Gly Phe Val Leu Met Phe Ile Ala Cys Ile
 65                  70                  75                  80

Val Trp Leu Lys Leu Val Ser Phe Ala His Thr Asn His Asp Ile Gly
                 85                  90                  95

Lys Leu Ile Thr Ser Gly Lys Lys Val Asp Asn Glu Leu Thr Ala Ala
            100                 105                 110

Gly Ile Asp Asn Leu Gln Xaa Pro Thr Leu Gly Ser Leu Thr Tyr Phe
        115                 120                 125

Lys Met Ala Pro Thr Leu Cys Tyr Gln Ala Lys Val Ile Leu Arg Thr
    130                 135                 140

Pro Tyr Val Arg Lys Gly Trp Leu Val Arg Gln Val Ile Leu Tyr Leu
145                 150                 155                 160

Ile Phe Thr Gly Leu Gln Gly Phe Ile Ile Glu Gln Tyr Ile Asn Pro
                165                 170                 175

Ile Val Val Asn Ser Gln His Pro Leu Met Gly Gly Leu Leu Asn Ala
            180                 185                 190

Val Glu Thr Val Leu Lys Leu Ser Leu Pro Asn Val Tyr Leu Trp Leu
        195                 200                 205

```
Cys Met Phe Tyr Cys Leu Phe His Leu Trp Leu Asn Ile Leu Ala Glu
    210                 215                 220

Ile Leu Arg Phe Gly Asp Arg Glu Phe Tyr Lys Asp Trp Asn Ala
225                 230                 235                 240

Lys Thr Ile Asp Glu Tyr Trp Arg Lys Trp Asn Met Pro Val His Lys
                245                 250                 255

Trp Ile Val Arg His Ile Tyr Phe Pro Cys Met Arg Asn Gly Ile Ser
            260                 265                 270

Lys Glu Val Ala Val Phe Ile Ser Phe Phe Val Ser Ala Val Leu His
        275                 280                 285

Glu Tyr Val Leu Leu Phe Leu His Ile Leu Lys Phe Trp Ala Phe Leu
290                 295                 300

Gly Ile Met Leu Gln Ile Pro Leu Ile Ile Leu Thr Ser Tyr Leu Lys
305                 310                 315                 320

Asn Lys Phe Ser Asp Thr Met Val Gly Asn Met Ile Phe Trp Phe Phe
                325                 330                 335

Phe Cys Ile Tyr Gly Gln Pro Met Cys Val Leu Leu Tyr Tyr His Asp
            340                 345                 350

Val Met Asn Arg Thr Glu Lys Ala Lys
            355                 360
```

```
<210> SEQ ID NO 5
<211> LENGTH: 978
<212> TYPE: DNA
<213> ORGANISM: Zea mays

<400> SEQUENCE: 5
ggcacgaggt tagaaaaggt tggctggtcc gtcaagttat tctatacttg atatttactg      60
gtctccaagg attcattatt gagcaataca taaatcctat tgttgtgaac tctcaacatc     120
cattgatggg aggattactg aatgctgtag agactgtttt gaagctctca ttaccaaatg     180
tctacctgtg gctttgcatg ttttattgcc ttttccatct gtggttaaac atacttgctg     240
agattcttcg atttggtgac cgagaattct acaaagactg gtggaatgca agacaattg      300
atgagtactg gagaaaatgg aacatgcctg tgcataaatg gattgttcgt catatatatt     360
tcccttgcat gcgaaatggt atatcaaagg aagttgctgt ttttatatcg ttctttgttt     420
ctgctgtact tcatgagctg cagattactt ggatgaagtg ctctatataa aattaaatat     480
ttcataatcc agtcccttc gagaaaatta tgtacattt tgtttgcaat tgtacaccag      540
ttatgtgttg ctgttccctg ccacatactc aagttctggg ctttcttagg aatcatgctt     600
cagattcccc tcatcatatt gacatcatac ctcaaaaata aattcagtga cacaatgcca     660
atgtgtgttc tattgtatta ccatgatgtg atgaaccgga ctgagaaggc aaaataacca     720
tctgtagatc ttttttggtg tttcatttct tccatcatgg aaactgaaag caataatctg     780
tgcacacagt aaaccagcat cgtgtcttcc agttttttt gttgttgttg gaatctatcc      840
tagatcttta tcatgtgtat ggtggataac ctcatgtcac catcgtatct gtatacaata     900
agcctaaatc agctgacgtt ctatatgtaa attagtaaat gtaatgacta attagtgcca     960
aaaaaaaaaa aaaaaaaa                                                  978
```

```
<210> SEQ ID NO 6
<211> LENGTH: 155
<212> TYPE: PRT
<213> ORGANISM: Zea mays

<400> SEQUENCE: 6
```

His Glu Val Arg Lys Gly Trp Leu Val Arg Gln Val Ile Leu Tyr Leu
1               5                   10                  15

Ile Phe Thr Gly Leu Gln Gly Phe Ile Ile Glu Gln Tyr Ile Asn Pro
            20                  25                  30

Ile Val Val Asn Ser Gln His Pro Leu Met Gly Gly Leu Asn Ala
            35                  40                  45

Val Glu Thr Val Leu Lys Leu Ser Leu Pro Asn Val Tyr Leu Trp Leu
    50                  55                  60

Cys Met Phe Tyr Cys Leu Phe His Leu Trp Leu Asn Ile Leu Ala Glu
65              70                  75                  80

Ile Leu Arg Phe Gly Asp Arg Glu Phe Tyr Lys Asp Trp Trp Asn Ala
                85                  90                  95

Lys Thr Ile Asp Glu Tyr Trp Arg Lys Trp Asn Met Pro Val His Lys
            100                 105                 110

Trp Ile Val Arg His Ile Tyr Phe Pro Cys Met Arg Asn Gly Ile Ser
            115                 120                 125

Lys Glu Val Ala Val Phe Ile Ser Phe Phe Val Ser Ala Val Leu His
130                 135                 140

Glu Leu Gln Ile Thr Trp Met Lys Cys Ser Ile
145                 150                 155

<210> SEQ ID NO 7
<211> LENGTH: 1559
<212> TYPE: DNA
<213> ORGANISM: Zea mays
<220> FEATURE:
<221> NAME/KEY: unsure
<222> LOCATION: (1542)..(1543)
<223> OTHER INFORMATION: n = a, c, g, or t
<220> FEATURE:
<221> NAME/KEY: unsure
<222> LOCATION: (1555)..(1556)
<223> OTHER INFORMATION: n = a, c, g, or t

<400> SEQUENCE: 7
ttttggttta atgctacatc attgcgagac tggccactgc taatgtgttg ccttagtcta      60
cccatatttc cccttggtgc atttgcagtc gaaaagttgg cattcaacaa tctcgttagt     120
gatcctgcta ctacctgttt tcacatcctt tttacaacat ttgaaattgt atatccagtg     180
ctcgtgattc ttaagtgtga ttctgcagtt ttatcaggct ttgtgttgat gtttattgcc     240
tgcattgttt ggctgaagct tgtatctttt gcacatacaa accatgatat aagaaaactg     300
atcacaagcg gcaagaaggt tgataatgaa ctgaccgcgg ctggcataga taatttacaa     360
gctccaactc ttgggagtct aacatacttc atgatggctc cgacactctg ttatcagcca     420
agttatcctc gaacacctta tgttagaaaa ggttggctgg tccgtcaagt tattctatac     480
ttgatattta ctggtctcca aggattcatt attgagcaat acataaatcc tattgttgtg     540
aactctcaac atccattgat gggaggatta ctgaatgctg tagagactgt tttgaagctc     600
tcattaccaa atgtctacct gtggctttgc atgtttatt gccttttcca tctgtggtta     660
aacatacttg ctgagattct tcgatttggt gaccgagaat tctacaaaga ctggtggaat     720
gcaaagacaa ttgatgagta ctggagaaaa tggaacatgc tgtgcataa atggattgtt     780 cgtcatatat attttccttg catgcgaaat ggtatatcaa aggaagttgc tgttttata     840 tcgttctttg tttctgctgt acttcatgag gtaacttatt acttttttca ctcttcatct     900
gcatatatta attatatagt tctctatttt caaatgtgtc ctttcgagtt tcgacatgct     960
tttgttcaaa cttaccagct gtagattact tggatgaagt gctctatata aaattcaata    1020

-continued

```
tttcacaatc cagtcccttt cgagaaaatt atgatacatt ttgtttgcat ttgtacacca    1080
gttatgcgtt gcagttccct gccacatact caagttctgg gctttcttag gaatcatgct    1140
tcagattccc ctcatcatat tgacatcata cctcaaaaat aaattcagtg acacaatggt    1200
tggcaatatg atcttttggt ttttttttctg catatacggg cagccaatgt gtgttctatt   1260
gtattaccat gatgtgatga accggactga aaggcaaaa taaccatctg tagatctttt     1320
ttggtgtttc atttctgcca tcatggaaac tgaaagcaat aatctgtgca cacagtaaac    1380
cagcatcgtg tcttccagtt ttcttttttgt tgttggaatc tatcctagat ctttatcatg   1440
tgtatggtgg ataacctcat gtcaccatcg tatctgtata caataagcct aaatcagctg    1500
acgttatata tgtataatta gtaaatgtag cgataaatgt cnncccccctg agagnnacg    1559
```

<210> SEQ ID NO 8
<211> LENGTH: 327
<212> TYPE: PRT
<213> ORGANISM: Zea mays

<400> SEQUENCE: 8

```
Phe Trp Phe Asn Ala Thr Ser Leu Arg Asp Trp Pro Leu Leu Met Cys
 1               5                  10                  15

Cys Leu Ser Leu Pro Ile Phe Pro Leu Gly Ala Phe Ala Val Glu Lys
                20                  25                  30

Leu Ala Phe Asn Asn Leu Val Ser Asp Pro Ala Thr Thr Cys Phe His
            35                  40                  45

Ile Leu Phe Thr Thr Phe Glu Ile Val Tyr Pro Val Leu Val Ile Leu
        50                  55                  60

Lys Cys Asp Ser Ala Val Leu Ser Gly Phe Val Leu Met Phe Ile Ala
    65                  70                  75                  80

Cys Ile Val Trp Leu Lys Leu Val Ser Phe Ala His Thr Asn His Asp
                85                  90                  95

Ile Arg Lys Leu Ile Thr Ser Gly Lys Lys Val Asp Asn Glu Leu Thr
            100                 105                 110

Ala Ala Gly Ile Asp Asn Leu Gln Ala Pro Thr Leu Gly Ser Leu Thr
        115                 120                 125

Tyr Phe Met Met Ala Pro Thr Leu Cys Tyr Gln Pro Ser Tyr Pro Arg
    130                 135                 140

Thr Pro Tyr Val Arg Lys Gly Trp Leu Val Arg Gln Val Ile Leu Tyr
145                 150                 155                 160

Leu Ile Phe Thr Gly Leu Gln Gly Phe Ile Glu Gln Tyr Ile Asn
                165                 170                 175

Pro Ile Val Val Asn Ser Gln His Pro Leu Met Gly Gly Leu Leu Asn
            180                 185                 190

Ala Val Glu Thr Val Leu Lys Leu Ser Leu Pro Asn Val Tyr Leu Trp
        195                 200                 205

Leu Cys Met Phe Tyr Cys Leu Phe His Leu Trp Leu Asn Ile Leu Ala
    210                 215                 220

Glu Ile Leu Arg Phe Gly Asp Arg Glu Phe Tyr Lys Asp Trp Trp Asn
225                 230                 235                 240

Ala Lys Thr Ile Asp Glu Tyr Trp Arg Lys Trp Asn Met Pro Val His
                245                 250                 255

Lys Trp Ile Val Arg His Ile Tyr Phe Pro Cys Met Arg Asn Gly Ile
            260                 265                 270

Ser Lys Glu Val Ala Val Phe Ile Ser Phe Phe Val Ser Ala Val Leu
        275                 280                 285
```

```
His Glu Val Thr Tyr Leu Leu Phe His Ser Ser Ala Tyr Ile Asn
    290                 295                 300

Tyr Ile Val Leu Tyr Phe Gln Met Cys Pro Phe Glu Phe Arg His Ala
305                 310                 315                 320

Phe Val Gln Thr Tyr Gln Leu
                325

<210> SEQ ID NO 9
<211> LENGTH: 901
<212> TYPE: DNA
<213> ORGANISM: Zea mays
<220> FEATURE:
<221> NAME/KEY: unsure
<222> LOCATION: (491)
<223> OTHER INFORMATION: n = a, c, g, or t
<220> FEATURE:
<221> NAME/KEY: unsure
<222> LOCATION: (577)
<223> OTHER INFORMATION: n = a, c, g, or t
<220> FEATURE:
<221> NAME/KEY: unsure
<222> LOCATION: (806)
<223> OTHER INFORMATION: n = a, c, g, or t
<220> FEATURE:
<221> NAME/KEY: unsure
<222> LOCATION: (893)
<223> OTHER INFORMATION: n = a, c, g, or t

<400> SEQUENCE: 9
ccggaattcc cgggtcgacc cacgcgtccg gtctcttatg cacatacaaa ttatgatata    60
agggtattgt ccaaaagtac tgagaagggt gctgcatatg gaaattatgt cgatcctgag   120
aatatgaaag atccaacctt taaagtcta gtgtacttca tgttggcccc aacactttgt    180
taccagccaa cttatcctca aactacatgt attagaaagg gttgggtgac ccagcaactc   240
ataaagtgcg tggttttttac aggcttgatg ggcttcataa ttgagcaata tataaaccca   300
attgtgaaga attccaaaca tccactgaaa gggaattttt tgaatgctat agaaagagtc   360
ttaaaactct cagtgccaac attatatgta tggctttgca tgttctattg cttttttcat   420
ttatggctga acattgtagc ttaactcctc tgtttcggtg accgtgaatt ctataaggac   480
tggtggaatg ncaaaactgt tgaagagtac tggaggatgt ggaacatgcc tgttcataag   540
tggatcatca gacacatata ttttccatgt ataaggnaag gcttttccag gggtgtagct   600
attctaatct cgtttctggg ttcagctgta ttccatgaga tatgtattgc ggtgccgtgc   660
cacattttca aattctgggc attttctggg atcatgtttc agataccgtt ggtattcttg   720
acaagatatc tccatgctac gttcaagcat gtaatggtgg gcaacatgat attttggttc   780
ttcagtatag tccgacagcc gatgtngtgt ctctataact aacatgacgt catgaaacaa   840
gcaaggccaa gcaagtagat agttcggcag agacatgtaa cttcaacatc gancatcaga   900
a                                                                  901

<210> SEQ ID NO 10
<211> LENGTH: 285
<212> TYPE: PRT
<213> ORGANISM: Zea mays
<220> FEATURE:
<221> NAME/KEY: UNSURE
<222> LOCATION: (148)
<223> OTHER INFORMATION: Xaa = ANY AMINO ACID
<220> FEATURE:
<221> NAME/KEY: UNSURE
<222> LOCATION: (164)
<223> OTHER INFORMATION: Xaa = ANY AMINO ACID
<220> FEATURE:
```

-continued

```
<221> NAME/KEY: UNSURE
<222> LOCATION: (193)
<223> OTHER INFORMATION: Xaa = ANY AMINO ACID
<220> FEATURE:
<221> NAME/KEY: UNSURE
<222> LOCATION: (269)
<223> OTHER INFORMATION: Xaa = ANY AMINO ACID
<220> FEATURE:
<221> NAME/KEY: UNSURE
<222> LOCATION: (274)
<223> OTHER INFORMATION: Xaa = ANY AMINO ACID

<400> SEQUENCE: 10

Pro Glu Phe Pro Gly Arg Pro Thr Arg Pro Val Ser Tyr Ala His Thr
 1               5                  10                  15

Asn Tyr Asp Ile Arg Val Leu Ser Lys Ser Thr Glu Lys Gly Ala Ala
            20                  25                  30

Tyr Gly Asn Tyr Val Asp Pro Glu Asn Met Lys Asp Pro Thr Phe Lys
        35                  40                  45

Ser Leu Val Tyr Phe Met Leu Ala Pro Thr Leu Cys Tyr Gln Pro Thr
    50                  55                  60

Tyr Pro Gln Thr Thr Cys Ile Arg Lys Gly Trp Val Thr Gln Gln Leu
65                  70                  75                  80

Ile Lys Cys Val Val Phe Thr Gly Leu Met Gly Phe Ile Ile Glu Gln
                85                  90                  95

Tyr Ile Asn Pro Ile Val Lys Asn Ser Lys His Pro Leu Lys Gly Asn
           100                 105                 110

Phe Leu Asn Ala Ile Glu Arg Val Leu Lys Leu Ser Val Pro Thr Leu
       115                 120                 125

Tyr Val Trp Leu Cys Met Phe Tyr Cys Phe Phe His Leu Trp Leu Asn
   130                 135                 140

Ile Val Ala Xaa Leu Leu Cys Phe Gly Asp Arg Glu Phe Tyr Lys Asp
145                 150                 155                 160

Trp Trp Asn Xaa Lys Thr Val Glu Glu Tyr Trp Arg Met Trp Asn Met
                165                 170                 175

Pro Val His Lys Trp Ile Ile Arg His Ile Tyr Phe Pro Cys Ile Arg
           180                 185                 190

Xaa Gly Phe Ser Arg Gly Val Ala Ile Leu Ile Ser Phe Leu Val Ser
       195                 200                 205

Ala Val Phe His Glu Ile Cys Ile Ala Val Pro Cys His Ile Phe Lys
   210                 215                 220

Phe Trp Ala Phe Ser Gly Ile Met Phe Gln Ile Pro Leu Val Phe Leu
225                 230                 235                 240

Thr Arg Tyr Leu His Ala Thr Phe Lys His Val Met Val Gly Asn Met
                245                 250                 255

Ile Phe Trp Phe Phe Ser Ile Val Arg Gln Pro Met Xaa Cys Leu Tyr
           260                 265                 270

Asn Xaa His Asp Val Met Lys Gln Ala Arg Pro Ser Lys
       275                 280                 285

<210> SEQ ID NO 11
<211> LENGTH: 254
<212> TYPE: DNA
<213> ORGANISM: Oryza sativa

<400> SEQUENCE: 11
ggcatacggc ggtggggact tctccgcgtt cacgttccgc gcggcggcgc cggtgcaccg      60
caaggccaag gagagccccc tcagctccga cgccatcttc aagcagagtc atgcaggcct     120
```

-continued

| | |
|---|---|
| tttcaaccta tgcattgttg ttctagttgc agtgaacagc aggcttatta tcgagaactt | 180 |
| aatgaagtat ggcttattaa taagagctgg gttttggttt aatgataaat cattgcggga | 240 |
| ctggccactt ctaa | 254 |

<210> SEQ ID NO 12
<211> LENGTH: 80
<212> TYPE: PRT
<213> ORGANISM: Oryza sativa

<400> SEQUENCE: 12

```
Ala Tyr Gly Gly Gly Asp Phe Ser Ala Phe Thr Phe Arg Ala Ala Ala
 1               5                  10                  15
Pro Val His Arg Lys Ala Lys Glu Ser Pro Leu Ser Ser Asp Ala Ile
            20                  25                  30
Phe Lys Gln Ser His Ala Gly Leu Phe Asn Leu Cys Ile Val Val Leu
        35                  40                  45
Val Ala Val Asn Ser Arg Leu Ile Ile Glu Asn Leu Met Lys Tyr Gly
    50                  55                  60
Leu Leu Ile Arg Ala Gly Phe Trp Phe Asn Asp Lys Ser Leu Arg Asp
65                  70                  75                  80
```

<210> SEQ ID NO 13
<211> LENGTH: 1587
<212> TYPE: DNA
<213> ORGANISM: Oryza sativa

<400> SEQUENCE: 13

| | |
|---|---|
| gcacgagggc atacggcggt ggggacttct ccgcgttcac gttccgcgcg cggcgccgg | 60 |
| tgcaccgcaa ggccaaggag agcccccctca gctccgacgc catcttcaag cagagtcatg | 120 |
| caggcctttt caacctatgc attgttgttc tagttgcagt gaacagcagg cttattatcg | 180 |
| agaacttaat gaagtatggc ttattaataa gagctgggtt ttggtttaat gataaatcat | 240 |
| tgcgggactg gccacttcta atgtgttgtc ttagtctgcc tgctttcccc ctgggtgcat | 300 |
| ttgcagttga aaagttggca tttaacaatg ttattactga tgctgttgct acctgcctcc | 360 |
| atatcttcct ttcaacaacc gaaattgtat atccagtgct tgtgattctt aagtgtgatt | 420 |
| ctgcagtttt gtctggcttt tgttgatat ttattgcctg tattgttttgg ctgaagcttg | 480 |
| tatcttttgc acatacaaac catgatataa ggcaactgac catgggcggc aagaaggttg | 540 |
| ataatgaact aagcacagtt gacatggata atttacaacc tccaacttta gggaatctaa | 600 |
| tatacttcat gatggctcct acactctgtt atcagccaag ctatccccga acttcatgtg | 660 |
| ttagaaaagg ttggctgatt cgtcaaatta ttctgtactt gatctttact ggtcttcaag | 720 |
| gcttcattat tgagcaatac ataaatccaa ttgttgtgaa ttctcagcat ccattgaaag | 780 |
| gaggactcct aaatgctgta gagactgttt tgaaactctc attaccaaat gtttacctgt | 840 |
| ggctttgcat gttctatgct ttttccatc tctggttaag tatacttgct gagattcttc | 900 |
| gatttggtga ccgtgaattc tacaaagatt ggtggaatgc aaaaacaatt gatgagtatt | 960 |
| ggagaaaatg gaatatgcct gtacataaat gggttgttcg ccatatttac tttccttgca | 1020 |
| tgcgaaatgg tatatcaaag gaagttgctg tcttgatatc attccttgtt tctgccgtac | 1080 |
| tccatgagat atgtgtcgct gttccctgcc gcattctcaa gttctgggca ttcttaggaa | 1140 |
| taatgctaca gatcccccctt atcgtattga cagcatacct caaaagtaaa ttcagagata | 1200 |
| caatggttgg caacatgata ttttggttct ttttctgcat ctatgggcag ccaatgtgcc | 1260 |
| ttctcctgta ctatcatgat gtgatgaaca ggattgagaa ggcaagataa atgcgtgttg | 1320 |

-continued

```
ccatctttt    cctctgtttc   attttgtacc   agcagaagca   caagcaataa   tccacatgct   1380
agccataaaa   cagcatgatt   cccaacggtg   tggtacagcc   aaccttcctg   ttattctatt   1440
ttcttggctg   tggtgtagat   ttagttttta   acttgtggct   aaccgcagga   atgcctgtag   1500
ataagcatct   gtcattctgt   ctggcgacgt   tctccttatt   aatgtgtaga   tgtagaactg   1560
tttccgaaaa   aaaaaaaaaa   aaaaaaa                                            1587
```

<210> SEQ ID NO 14
<211> LENGTH: 500
<212> TYPE: PRT
<213> ORGANISM: Oryza sativa

<400> SEQUENCE: 14

| Met | Val | Gly | Ser | Asp | Gly | Asp | Gly | Asp | Gly | Gly | Gly | Glu | Ala | His |
|---|---|---|---|---|---|---|---|---|---|---|---|---|---|---|
| 1 | | | | 5 | | | | | 10 | | | | | 15 |

| Ala | Gly | Gly | Pro | Arg | Arg | Ala | Gly | Gln | Leu | Arg | Gly | Arg | Leu | Arg |
| | | | 20 | | | | | 25 | | | | | 30 | |

| Asp | Glu | Ala | Ala | Pro | Gly | Ser | Pro | Arg | Pro | Arg | Pro | Arg | Pro | Arg |
| | | 35 | | | | | 40 | | | | | 45 | | |

| Pro | Arg | Gly | Gly | Asp | Ser | Asn | Gly | Arg | Ser | Val | Leu | Arg | Pro | Gly | Gly |
| | 50 | | | | | 55 | | | | | 60 | | | | |

| Gly | Gly | Gly | Arg | Gly | Gly | Gly | Asp | Phe | Ser | Ala | Phe | Thr | Phe | Arg |
| 65 | | | | | 70 | | | | | 75 | | | | | 80 |

| Ala | Ala | Ala | Pro | Val | His | Arg | Lys | Ala | Lys | Glu | Ser | Pro | Leu | Ser | Ser |
| | | | | 85 | | | | | 90 | | | | | 95 | |

| Asp | Ala | Ile | Phe | Lys | Gln | Ser | His | Ala | Gly | Leu | Phe | Asn | Leu | Cys | Ile |
| | | | 100 | | | | | 105 | | | | | 110 | | |

| Val | Val | Leu | Val | Ala | Val | Asn | Ser | Arg | Leu | Ile | Ile | Glu | Asn | Leu | Met |
| | | 115 | | | | | 120 | | | | | 125 | | | |

| Lys | Tyr | Gly | Leu | Leu | Ile | Arg | Ala | Gly | Phe | Trp | Phe | Asn | Asp | Lys | Ser |
| | 130 | | | | | 135 | | | | | 140 | | | | |

| Leu | Arg | Asp | Trp | Pro | Leu | Leu | Met | Cys | Cys | Leu | Ser | Leu | Pro | Ala | Phe |
| 145 | | | | | 150 | | | | | 155 | | | | | 160 |

| Pro | Leu | Gly | Ala | Phe | Ala | Val | Glu | Lys | Leu | Ala | Phe | Asn | Asn | Val | Ile |
| | | | | 165 | | | | | 170 | | | | | 175 | |

| Thr | Asp | Ala | Val | Ala | Thr | Cys | Leu | His | Ile | Phe | Leu | Ser | Thr | Thr | Glu |
| | | | 180 | | | | | 185 | | | | | 190 | | |

| Ile | Val | Tyr | Pro | Val | Leu | Val | Ile | Leu | Lys | Cys | Asp | Ser | Ala | Val | Leu |
| | | 195 | | | | | 200 | | | | | 205 | | | |

| Ser | Gly | Phe | Leu | Leu | Ile | Phe | Ile | Ala | Cys | Ile | Val | Trp | Leu | Lys | Leu |
| | 210 | | | | | 215 | | | | | 220 | | | | |

| Val | Ser | Phe | Ala | His | Thr | Asn | His | Asp | Ile | Arg | Gln | Leu | Thr | Met | Gly |
| 225 | | | | | 230 | | | | | 235 | | | | | 240 |

| Gly | Lys | Lys | Val | Asp | Asn | Glu | Leu | Ser | Thr | Val | Asp | Met | Asp | Asn | Leu |
| | | | | 245 | | | | | 250 | | | | | 255 | |

| Gln | Pro | Pro | Thr | Leu | Gly | Asn | Leu | Ile | Tyr | Phe | Met | Met | Ala | Pro | Thr |
| | | | 260 | | | | | 265 | | | | | 270 | | |

| Leu | Cys | Tyr | Gln | Pro | Ser | Tyr | Pro | Arg | Thr | Ser | Cys | Val | Arg | Lys | Gly |
| | | 275 | | | | | 280 | | | | | 285 | | | |

| Trp | Leu | Ile | Arg | Gln | Ile | Ile | Tyr | Leu | Ile | Phe | Thr | Gly | Leu | Gln |
| | 290 | | | | | 295 | | | | | 300 | | | |

| Gly | Phe | Ile | Ile | Glu | Gln | Tyr | Ile | Asn | Pro | Ile | Val | Val | Asn | Ser | Gln |
| 305 | | | | | 310 | | | | | 315 | | | | | 320 |

| His | Pro | Leu | Lys | Gly | Gly | Leu | Leu | Asn | Ala | Val | Glu | Thr | Val | Leu | Lys |

```
                    325                 330                 335
Leu Ser Leu Pro Asn Val Tyr Leu Trp Leu Cys Met Phe Tyr Ala Phe
            340                 345                 350

Phe His Leu Trp Leu Ser Ile Leu Ala Glu Ile Leu Arg Phe Gly Asp
        355                 360                 365

Arg Glu Phe Tyr Lys Asp Trp Trp Asn Ala Lys Thr Ile Asp Glu Tyr
    370                 375                 380

Trp Arg Lys Trp Asn Met Pro Val His Lys Trp Val Val Arg His Ile
385                 390                 395                 400

Tyr Phe Pro Cys Met Arg Asn Gly Ile Ser Lys Glu Val Ala Val Leu
                405                 410                 415

Ile Ser Phe Leu Val Ser Ala Val Leu His Glu Ile Cys Val Ala Val
            420                 425                 430

Pro Cys Arg Ile Leu Lys Phe Trp Ala Phe Leu Gly Ile Met Leu Gln
        435                 440                 445

Ile Pro Leu Ile Val Leu Thr Ala Tyr Leu Lys Ser Lys Phe Arg Asp
    450                 455                 460

Thr Met Val Gly Asn Met Ile Phe Trp Phe Phe Cys Ile Tyr Gly
465                 470                 475                 480

Gln Pro Met Cys Leu Leu Leu Tyr Tyr His Asp Val Met Asn Arg Ile
                485                 490                 495

Glu Lys Ala Arg
            500

<210> SEQ ID NO 15
<211> LENGTH: 1942
<212> TYPE: DNA
<213> ORGANISM: Glycine max

<400> SEQUENCE: 15
tagaaaacac gctcggtctt cttctccaat ggcgatttcc gatgagcctg aaagtgtagc    60
cactgctctc aaccactctt ccctgcgccg ccgtccctcc gccacctcca ccgccggcct   120
cttcaattcg cctgagacaa ccaccgacag ttccggtgat gacttggcca aggattctgg   180
ttccgacgac tccatcaaca gcgacgacgc cgccgtcaat tcccaacagc aaaacgaaaa   240
acaagacact gatttctccg tcctcaaatt cgcctaccgt ccttccgtcc cgctcaccg   300 caaagtgaag gaaagtccgc tcagctccga cactattttc cgtcagagtc acgcgggcct   360
cttcaacctt tgtatagtag tccttgttgc tgtgaatagc cgactcatca ttgagaattt   420
aatgaagtat ggttggttga tcaaatctgg cttttggttt agttcaaagt cattgagaga   480
ctggcccctt ttcatgtgtt gtctttctct tgtggtattt cctttcgctg cctttatagt   540
ggagaagttg gcacaacgga agtgtatacc cgaaccagtt gttgttgtac ttcatataat   600
cattacctca acttcgcttt tctatccagt tttagttatt ctcaggtgtg attctgcttt   660
tgtatcaggt gtcacgttaa tgctgttttc ttgtgttgta tggttaaaat tggtgtctta   720
tgcatataca aactatgata tgagagcact taccaaatta gttgaaaagg gagaagcact   780
gctcgatact ctgaacatgg actatcctta caacgtaagc ttcaagagct ggcatattt   840 cctggttgcc cctacattat gttaccagcc aagctatcct cgcacacctt atattcgaaa   900
gggttggttg tttcgccaac ttgtcaagct gataatattt acaggagtta tgggattat   960 aatagaccaa tatattaatc ccatagtaca aaattcacag catcctctca agggaaacct  1020
tctttacgcc accgagagag ttctgaagct ttctgttcca aatttatatg tgtggctctg  1080
catgttctat tgcttttctc acctttggtt aaatatcctg gcagagcttc ttcgatttgg  1140
```

```
tgatcgtgaa ttctacaagg attggtggaa tgccaaaact gtcgaagatt attggaggat   1200
gtggaatatg cctgttcaca aatggatgat ccgccaccta tattttccat gtttaaggca   1260
cggtctacca aaggctgctg ctcttttaat tgccttcctg gtttctgctt tattccatga   1320
gctgtgcatt gctgttcctt gccacatatt caagttgtgg gctttcggtg gaattatgtt   1380
tcaggttcct ttggtcttga tcactaatta tctgcaaaat aaattcagaa actcaatggt   1440
tggaaatatg atttttggt tcatattcag tatccttggt caacctatgt gtgtactgct   1500
atactaccat gacttgatga ataggaaagg caaacttgac tgaagctacg gccattacat   1560 tttaaggtg cacatggatg agcttttcag ttttcagatt gtaaaattga tgtggatatg   1620
ttggtcaata tttgttttct acgaatgctt tcatctacca tggcattggc tgctctgaag   1680
gaattccacg ggatatgcca gttcacgagg ctaattcatt atcttgatct atgtacttac   1740
caactctcct ctggcaattg tatcaaaata tgcaattttg agagccatac actggcattg   1800
ataactgcca aggaacactc taactgtttt ctgttaactg ttaattagta gagggctaga   1860
tgtaaatggt ttatgctcaa tatatttatt tcctcctaaa aaaaaaaaa aaaaaaaaa    1920 aaaaaaaaaa aaaaaaaaaa aa                                           1942
```

<210> SEQ ID NO 16
<211> LENGTH: 504
<212> TYPE: PRT
<213> ORGANISM: Glycine max

<400> SEQUENCE: 16

```
Met Ala Ile Ser Asp Glu Pro Glu Ser Val Ala Thr Ala Leu Asn His
  1               5                  10                  15

Ser Ser Leu Arg Arg Pro Ser Ala Thr Ser Thr Ala Gly Leu Phe
             20                  25                  30

Asn Ser Pro Glu Thr Thr Thr Asp Ser Ser Gly Asp Asp Leu Ala Lys
         35                  40                  45

Asp Ser Gly Ser Asp Asp Ser Ile Asn Ser Asp Ala Ala Val Asn
     50                  55                  60

Ser Gln Gln Gln Asn Glu Lys Gln Asp Thr Asp Phe Ser Val Leu Lys
 65                  70                  75                  80

Phe Ala Tyr Arg Pro Ser Val Pro Ala His Arg Lys Val Lys Glu Ser
                 85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
    130                 135                 140

Ser Ser Lys Ser Leu Arg Asp Trp Pro Leu Phe Met Cys Cys Leu Ser
145                 150                 155                 160

Leu Val Val Phe Pro Phe Ala Ala Phe Ile Val Glu Lys Leu Ala Gln
                165                 170                 175

Arg Lys Cys Ile Pro Glu Pro Val Val Val Leu His Ile Ile Ile
            180                 185                 190

Thr Ser Thr Ser Leu Phe Tyr Pro Val Leu Val Ile Leu Arg Cys Asp
        195                 200                 205

Ser Ala Phe Val Ser Gly Val Thr Leu Met Leu Phe Ser Cys Val Val
    210                 215                 220

Trp Leu Lys Leu Val Ser Tyr Ala His Thr Asn Tyr Asp Met Arg Ala
```

-continued

```
            225                 230                 235                 240
Leu Thr Lys Leu Val Glu Lys Gly Glu Ala Leu Leu Asp Thr Leu Asn
                245                 250                 255

Met Asp Tyr Pro Tyr Asn Val Ser Phe Lys Ser Leu Ala Tyr Phe Leu
            260                 265                 270

Val Ala Pro Thr Leu Cys Tyr Gln Pro Ser Tyr Pro Arg Thr Pro Tyr
        275                 280                 285

Ile Arg Lys Gly Trp Leu Phe Arg Gln Leu Val Lys Leu Ile Ile Phe
    290                 295                 300

Thr Gly Val Met Gly Phe Ile Ile Asp Gln Tyr Ile Asn Pro Ile Val
305                 310                 315                 320

Gln Asn Ser Gln His Pro Leu Lys Gly Asn Leu Leu Tyr Ala Thr Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Arg Phe Gly Asp Arg Glu Phe Tyr Lys Asp Trp Trp Asn Ala Lys Thr
    370                 375                 380

Val Glu Asp Tyr Trp Arg Met Trp Asn Met Pro Val His Lys Trp Met
385                 390                 395                 400

Ile Arg His Leu Tyr Phe Pro Cys Leu Arg His Gly Leu Pro Lys Ala
                405                 410                 415

Ala Ala Leu Leu Ile Ala Phe Leu Val Ser Ala Leu Phe His Glu Leu
            420                 425                 430

Cys Ile Ala Val Pro Cys His Ile Phe Lys Leu Trp Ala Phe Gly Gly
        435                 440                 445

Ile Met Phe Gln Val Pro Leu Val Leu Ile Thr Asn Tyr Leu Gln Asn
    450                 455                 460

Lys Phe Arg Asn Ser Met Val Gly Asn Met Ile Phe Trp Phe Ile Phe
465                 470                 475                 480

Ser Ile Leu Gly Gln Pro Met Cys Val Leu Leu Tyr Tyr His Asp Leu
                485                 490                 495

Met Asn Arg Lys Gly Lys Leu Asp
            500

<210> SEQ ID NO 17
<211> LENGTH: 470
<212> TYPE: DNA
<213> ORGANISM: Glycine max
<220> FEATURE:
<221> NAME/KEY: unsure
<222> LOCATION: (372)
<223> OTHER INFORMATION: n = a, c, g, or t
<220> FEATURE:
<221> NAME/KEY: unsure
<222> LOCATION: (424)
<223> OTHER INFORMATION: n = a, c, g, or t
<220> FEATURE:
<221> NAME/KEY: unsure
<222> LOCATION: (442)
<223> OTHER INFORMATION: n = a, c, g, or t
<220> FEATURE:
<221> NAME/KEY: unsure
<222> LOCATION: (446)
<223> OTHER INFORMATION: n = a, c, g, or t
<220> FEATURE:
<221> NAME/KEY: unsure
<222> LOCATION: (469)
<223> OTHER INFORMATION: n = a, c, g, or t

<400> SEQUENCE: 17
```

```
taaacacgct cgctcggtct tcttttccaa tggcgatttc cgatgagcct gaaactgtag    60
ccactgctct caaccactct tccctgcgcc gccgtcccac cgccgctggc ctcttcaatt   120
cgcccgagac gaccaccgac agttccggtg atgacttggc caaggattcc ggttccgacg   180
actccatcag cagcgacgcc gccaattcgc aaccgcaaca aaaacaagac actgatttct   240
ccgtcctcaa attcgcctac cgtccttccg tccccgctca tcgcaaagtg aaggaaagtc   300
cgctcagctc ccgacaccat tttccgtcag aagtcacgcg gggcctcttc aacctcctgt   360
atagtaagtc cntgttgctg tgaataagcc gactcatcat tgagaatttt aaatgaaata   420
tggnttgggt tgatcaaatc cnggcntttt gggttaagct caaagtcant              470
```

<210> SEQ ID NO 18
<211> LENGTH: 38
<212> TYPE: PRT
<213> ORGANISM: Glycine max

<400> SEQUENCE: 18

Asp Phe Ser Val Leu Lys Phe Ala Tyr Arg Pro Ser Val Pro Ala His
 1               5                  10                  15

Arg Lys Val Lys Glu Ser Pro Leu Ser Ser Asp Thr Ile Phe Val Arg
            20                  25                  30

Ser His Ala Gly Pro Leu
        35

<210> SEQ ID NO 19
<211> LENGTH: 646
<212> TYPE: DNA
<213> ORGANISM: Triticum aestivum
<220> FEATURE:
<221> NAME/KEY: unsure
<222> LOCATION: (240)
<223> OTHER INFORMATION: n = a, c, g, or t
<220> FEATURE:
<221> NAME/KEY: unsure
<222> LOCATION: (311)
<223> OTHER INFORMATION: n = a, c, g, or t
<220> FEATURE:
<221> NAME/KEY: unsure
<222> LOCATION: (337)
<223> OTHER INFORMATION: n = a, c, g, or t
<220> FEATURE:
<221> NAME/KEY: unsure
<222> LOCATION: (354)
<223> OTHER INFORMATION: n = a, c, g, or t
<220> FEATURE:
<221> NAME/KEY: unsure
<222> LOCATION: (370)
<223> OTHER INFORMATION: n = a, c, g, or t
<220> FEATURE:
<221> NAME/KEY: unsure
<222> LOCATION: (383)
<223> OTHER INFORMATION: n = a, c, g, or t
<220> FEATURE:
<221> NAME/KEY: unsure
<222> LOCATION: (388)
<223> OTHER INFORMATION: n = a, c, g, or t
<220> FEATURE:
<221> NAME/KEY: unsure
<222> LOCATION: (423)
<223> OTHER INFORMATION: n = a, c, g, or t
<220> FEATURE:
<221> NAME/KEY: unsure
<222> LOCATION: (431)
<223> OTHER INFORMATION: n = a, c, g, or t
<220> FEATURE:
<221> NAME/KEY: unsure
<222> LOCATION: (435)
<223> OTHER INFORMATION: n = a, c, g, or t
<220> FEATURE:

```
<221> NAME/KEY: unsure
<222> LOCATION: (463)
<223> OTHER INFORMATION: n = a, c, g, or t
<220> FEATURE:
<221> NAME/KEY: unsure
<222> LOCATION: (486)
<223> OTHER INFORMATION: n = a, c, g, or t
<220> FEATURE:
<221> NAME/KEY: unsure
<222> LOCATION: (503)
<223> OTHER INFORMATION: n = a, c, g, or t
<220> FEATURE:
<221> NAME/KEY: unsure
<222> LOCATION: (540)
<223> OTHER INFORMATION: n = a, c, g, or t
<220> FEATURE:
<221> NAME/KEY: unsure
<222> LOCATION: (547)
<223> OTHER INFORMATION: n = a, c, g, or t
<220> FEATURE:
<221> NAME/KEY: unsure
<222> LOCATION: (616)
<223> OTHER INFORMATION: n = a, c, g, or t
<220> FEATURE:
<221> NAME/KEY: unsure
<222> LOCATION: (633)
<223> OTHER INFORMATION: n = a, c, g, or t
<220> FEATURE:
<221> NAME/KEY: unsure
<222> LOCATION: (639)
<223> OTHER INFORMATION: n = a, c, g, or t

<400> SEQUENCE: 19
ctccgacgcc atcttccgac agagccatgc aggtcttctg aatctatgca ttgttgtgct    60
gattgcagtg aacagcaggc tcattattga gaacttaatg aagtatggcc tattaataag   120
agctgggttt tggtttaagt gcaagatcgc tgggagattg gccacttctg atgtgctgcc   180
tcactttacc cattttccca cttgctgctc tcatgaccgg agaattgggt caaagaaaan   240
tcatccgtgg atcatgtgtc tatcctcccc catataatta ttacaaccac tgtccttatc   300
ctatccggtg ntgtgatcct taaagtgtga accacantat atcctggttt gtgnttatgt   360
ccattgcaan atacttgggt ganctttgncc cttttgctcc atacaattag atataagtat   420 tgncccccaaa ntatngaaag ggtgctacac agggattcta ccnagaagaa aattaaagcc   480
caactncaac aagtgtgtat cangttggcc caacactggt acaaccaatt tacccggcan   540
attatanaaa ggtggtcacc ggaactataa agtgtatttt aagcttatgg ctcaaatggc   600
ataataacca ttgganatca acacatgacg aanttttgnc atgaaa                  646

<210> SEQ ID NO 20
<211> LENGTH: 39
<212> TYPE: PRT
<213> ORGANISM: Triticum aestivum

<400> SEQUENCE: 20

Ser Asp Ala Ile Phe Arg Gln Ser His Ala Gly Leu Leu Asn Leu Cys
 1               5                  10                  15

Ile Val Val Leu Ile Ala Val Asn Ser Arg Leu Ile Ile Glu Asn Leu
            20                  25                  30

Met Lys Tyr Gly Leu Leu Ile
        35

<210> SEQ ID NO 21
<211> LENGTH: 1975
<212> TYPE: DNA
<213> ORGANISM: Triticum aestivum
<220> FEATURE:
<221> NAME/KEY: unsure
```

<222> LOCATION: (93)
<223> OTHER INFORMATION: n = a, c, g, or t

<400> SEQUENCE: 21

```
acgagggcct aggtcgcctc cgcsactgtg tcagcgcgca agtcggccgc ctccctccgc    60
tttmcgcttt tgcgcgtcmg tgctggcgcg ggnccaccac catcgcatgt caaaagggaa   120
cccagacccg cacctccccg gcagcttcct cccttcccac ggcgggccgc caccgaaacc   180
caaaaccccg ccccgaacct tccggaacct ccctccagt tccacccatg gccccgcccc    240
gtccgtggcc gctgccacga tcgcgacgac ccctccctcc gctccgccg cgcccctgcc    300
gccgacggtc cacggagagg cggcgcatgg agcagccgca gcggcacgac gagatgccct   360
gctaccgggc gtcggcgccg cccaccgccg ggtcaaggag agcccgctta gctccgacgc   420
catcttccga cagagccatg caggtcttct gaatctatgc attgttgtgc tgattgcagt   480
gaacagcagg ctcattatcg agaacttaat gaagtatggc ctattaataa gagctgggtt   540
ttggtttagt gcaagatcgc tgggagattg gccacttctg atgtgctgcc tcactttacc   600
cattttccca cttgctgctc tcatgaccga gaagtgggct caaagaaagc tcatccgtga   660
tcatgtgtct attcttctcc atataattat tacaaccact gtccttatct atccggttgt   720
tgtgattctt aagtgtgaat cagcagtatt atctggattt tgttaatgt tcattgcaag    780
cattacttgg ttgaagcttg tctcttttgc tcatacaaat tatgatataa ggatattgtc   840
ccaaagtatt gaaaagggtg ctacacatgg cagttctatc gatgaggaaa acattaaagg   900
cccaactatc aacagtgttg tgtatttcat gttggcccca acactttgtt accagccaag   960
ttatccccgg acagcattta ttagaaaagg ctgggtcacc cggcagctta taaaatgtgt  1020
agttttaca ggcttgatgg gcttcataat tgagcaatac attaatccaa ttgtgcagaa   1080
ttcgaagcat ccattgaacg gaaatttctt ggatgctatt gagagagtct tgaaactctc  1140
agtgccaaca ttatatgtat ggctttgtat gttctattcc tttttccatc tgtggttgaa  1200
tattctagcc gaactcctcc gttttggtga tcgtgaattc tacaaggact ggtggaacgc  1260
caaaacagtt gaagagtact ggagaatgtg gaatatgcct gttcataagt ggatcgttcg  1320
acatatatat tttccatgca taaggaatgg cttatcaaag ggttgtgcca ttctcatcgc  1380
atttctggtt tcagctgtat ttcatgagct atgtattgct gttccgtgcc acattttcaa  1440
attatgggca ttttctggaa tcatgtttca gattcccctg ctattcttga cgaaatatct  1500
tcaagataag ttcaagaata caatggtggg caacatgata ttttggttct tcttcagcat  1560
agttgggcaa ccaatgtgtg ttctcttgta ctaccatgat gtcatgaaca gacaggctca  1620
gacaaatggc tagttctgtt ttagaagtgc actataacac agatcgtccg aagcaaattg  1680
gcccgaggca atggaggggc ggcctcctta atgtttcgcc atgggctgtt agagcttgct  1740
atgctacgaa tccaagtttg tcagcatgat atgttccaat ccgttccagt tagctcgctg  1800
cgttccaaat gtatgatatg ccggccgggg tgtgtaccga agataccca gtgatgaagc    1860
cgaagataac acgacctgcc acatgtgttt tgtgtatacg tttcggttca tgtgccagca  1920
gagttacgta cgtgatgccc tgttggatat aaagtgtacg tgccgtatga aaaa         1975
```

<210> SEQ ID NO 22
<211> LENGTH: 508
<212> TYPE: PRT
<213> ORGANISM: Triticum aestivum

<400> SEQUENCE: 22

Met Ser Lys Gly Asn Pro Asp Pro His Leu Pro Gly Ser Phe Leu Pro

```
            1               5                  10                 15
Ser His Gly Gly Pro Pro Lys Pro Lys Thr Pro Pro Arg Thr Phe
                20                  25                  30

Arg Asn Leu Pro Ser Ser Thr His Gly Pro Ala Pro Ser Val Ala
                35                  40                  45

Ala Ala Thr Ile Ala Thr Thr Pro Pro Ser Ala Ser Ala Ala Pro Leu
            50                  55                  60

Pro Pro Thr Val His Gly Glu Ala Ala His Gly Ala Ala Ala Ala
65                  70                  75                  80

Arg Arg Asp Ala Leu Leu Pro Gly Val Gly Ala Ala His Arg Val
                85                  90                  95

Lys Glu Ser Pro Leu Ser Ser Asp Ala Ile Phe Arg Gln Ser His Ala
                100                 105                 110

Gly Leu Leu Asn Leu Cys Ile Val Val Leu Ile Ala Val Asn Ser Arg
                115                 120                 125

Leu Ile Ile Glu Asn Leu Met Lys Tyr Gly Leu Leu Ile Arg Ala Gly
                130                 135                 140

Phe Trp Phe Ser Ala Arg Ser Leu Gly Asp Trp Pro Leu Leu Met Cys
145                 150                 155                 160

Cys Leu Thr Leu Pro Ile Phe Pro Leu Ala Ala Leu Met Thr Glu Lys
                165                 170                 175

Trp Ala Gln Arg Lys Leu Ile Arg Asp His Val Ser Ile Leu Leu His
                180                 185                 190

Ile Ile Ile Thr Thr Thr Val Leu Ile Tyr Pro Val Val Val Ile Leu
                195                 200                 205

Lys Cys Glu Ser Ala Val Leu Ser Gly Phe Val Leu Met Phe Ile Ala
210                 215                 220

Ser Ile Thr Trp Leu Lys Leu Val Ser Phe Ala His Thr Asn Tyr Asp
225                 230                 235                 240

Ile Arg Ile Leu Ser Gln Ser Ile Glu Lys Gly Ala Thr His Gly Ser
                245                 250                 255

Ser Ile Asp Glu Glu Asn Ile Lys Gly Pro Thr Ile Asn Ser Val Val
                260                 265                 270

Tyr Phe Met Leu Ala Pro Thr Leu Cys Tyr Gln Pro Ser Tyr Pro Arg
                275                 280                 285

Thr Ala Phe Ile Arg Lys Gly Trp Val Thr Arg Gln Leu Ile Lys Cys
                290                 295                 300

Val Val Phe Thr Gly Leu Met Gly Phe Ile Ile Glu Gln Tyr Ile Asn
305                 310                 315                 320

Pro Ile Val Gln Asn Ser Lys His Pro Leu Asn Gly Asn Phe Leu Asp
                325                 330                 335

Ala Ile Glu Arg Val Leu Lys Leu Ser Val Pro Thr Leu Tyr Val Trp
                340                 345                 350

Leu Cys Met Phe Tyr Ser Phe Phe His Leu Trp Leu Asn Ile Leu Ala
                355                 360                 365

Glu Leu Leu Arg Phe Gly Asp Arg Glu Phe Tyr Lys Asp Trp Trp Asn
                370                 375                 380

Ala Lys Thr Val Glu Glu Tyr Trp Arg Met Trp Asn Met Pro Val His
385                 390                 395                 400

Lys Trp Ile Val Arg His Ile Tyr Phe Pro Cys Ile Arg Asn Gly Leu
                405                 410                 415

Ser Lys Gly Cys Ala Ile Leu Ile Ala Phe Leu Val Ser Ala Val Phe
                420                 425                 430
```

```
His Glu Leu Cys Ile Ala Val Pro Cys His Ile Phe Lys Leu Trp Ala
        435                 440                 445

Phe Ser Gly Ile Met Phe Gln Ile Pro Leu Leu Phe Leu Thr Lys Tyr
    450                 455                 460

Leu Gln Asp Lys Phe Lys Asn Thr Met Val Gly Asn Met Ile Phe Trp
465                 470                 475                 480

Phe Phe Phe Ser Ile Val Gly Gln Pro Met Cys Val Leu Leu Tyr Tyr
                485                 490                 495

His Asp Val Met Asn Arg Gln Ala Gln Thr Asn Gly
                500                 505

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 23
cttagcttct tccttcaatc                                            20

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence:PCR primer

<400> SEQUENCE: 24
tttctagact cgagtgaaca gttgtttcat gac                             33

<210> SEQ ID NO 25
<211> LENGTH: 497
<212> TYPE: PRT
<213> ORGANISM: Mus musculus

<400> SEQUENCE: 25

Met Gly Asp Arg Gly Gly Ala Gly Ser Ser Arg Arg Thr Gly Ser
  1               5                  10                  15

Arg Val Ser Val Gln Gly Gly Ser Gly Pro Lys Val Glu Glu Asp Glu
                 20                  25                  30

Val Arg Asp Ala Ala Val Ser Pro Asp Leu Gly Ala Gly Asp Ala
             35                  40                  45

Pro Ala Pro Ala Pro Ala Pro Ala His Thr Arg Asp Lys Asp Gly Arg
     50                  55                  60

Thr Ser Val Gly Asp Gly Tyr Trp Asp Leu Arg Cys His Arg Leu Gln
 65                  70                  75                  80

Asp Ser Leu Phe Ser Ser Asp Ser Gly Phe Ser Asn Tyr Arg Gly Ile
                 85                  90                  95

Leu Asn Trp Cys Val Val Met Leu Ile Leu Ser Asn Ala Arg Leu Phe
                100                 105                 110

Leu Glu Asn Leu Ile Lys Tyr Gly Ile Leu Val Asp Pro Ile Gln Val
             115                 120                 125

Val Ser Leu Phe Leu Lys Asp Pro Tyr Ser Trp Pro Ala Pro Cys Val
130                 135                 140

Ile Ile Ala Ser Asn Ile Phe Val Val Ala Ala Phe Gln Ile Glu Lys
145                 150                 155                 160

Arg Leu Ala Val Gly Ala Leu Thr Glu Gln Met Gly Leu Leu Leu His
                165                 170                 175
```

-continued

```
Val Val Asn Leu Ala Thr Ile Ile Cys Phe Pro Ala Ala Val Ala Leu
            180                 185                 190

Leu Val Glu Ser Ile Thr Pro Val Gly Ser Val Phe Ala Leu Ala Ser
        195                 200                 205

Tyr Ser Ile Met Phe Leu Lys Leu Tyr Ser Tyr Arg Asp Val Asn Leu
    210                 215                 220

Trp Cys Arg Gln Arg Arg Val Lys Ala Lys Ala Val Ser Thr Gly Lys
225                 230                 235                 240

Lys Val Ser Gly Ala Ala Gln Gln Ala Val Ser Tyr Pro Asp Asn
                245                 250                 255

Leu Thr Tyr Arg Asp Leu Tyr Tyr Phe Ile Phe Ala Pro Thr Leu Cys
            260                 265                 270

Tyr Glu Leu Asn Phe Pro Arg Ser Pro Arg Ile Arg Lys Arg Phe Leu
        275                 280                 285

Leu Arg Arg Val Leu Glu Met Leu Phe Phe Thr Gln Leu Gln Val Gly
    290                 295                 300

Leu Ile Gln Gln Trp Met Val Pro Thr Ile His Asn Ser Met Lys Pro
305                 310                 315                 320

Phe Lys Asp Met Asp Tyr Ser Arg Ile Ile Glu Arg Leu Leu Lys Leu
                325                 330                 335

Ala Val Pro Asn His Leu Ile Trp Leu Ile Phe Phe Tyr Trp Phe Phe
            340                 345                 350

His Ser Cys Leu Asn Ala Val Ala Glu Leu Leu Gln Phe Gly Asp Arg
        355                 360                 365

Glu Phe Tyr Arg Asp Trp Trp Asn Ala Glu Ser Val Thr Tyr Phe Trp
    370                 375                 380

Gln Asn Trp Asn Ile Pro Val His Lys Trp Cys Ile Arg His Phe Tyr
385                 390                 395                 400

Lys Pro Met Leu Arg His Gly Ser Ser Lys Trp Val Ala Arg Thr Gly
                405                 410                 415

Val Phe Leu Thr Ser Ala Phe Phe His Glu Tyr Leu Val Ser Val Pro
            420                 425                 430

Leu Arg Met Phe Arg Leu Trp Ala Phe Thr Ala Met Met Ala Gln Val
        435                 440                 445

Pro Leu Ala Trp Ile Val Gly Arg Phe Phe Gln Gly Asn Tyr Gly Asn
    450                 455                 460

Ala Ala Val Trp Val Thr Leu Ile Ile Gly Gln Pro Val Ala Val Leu
465                 470                 475                 480

Met Tyr Val His Asp Tyr Tyr Val Leu Asn Tyr Asp Ala Pro Val Gly
                485                 490                 495

Val

<210> SEQ ID NO 26
<211> LENGTH: 520
<212> TYPE: PRT
<213> ORGANISM: Arabidopsis thaliana

<400> SEQUENCE: 26

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
```

```
              50                  55                  60
Ser Val Val Asn Asp Asp Ala Gln Gly Thr Ala Asn Leu Ala Gly Asp
 65                  70                  75                  80

Asn Asn Gly Gly Gly Asp Asn Asn Gly Gly Arg Gly Gly Gly Glu
                 85                  90                  95

Gly Arg Gly Asn Ala Asp Ala Thr Phe Thr Tyr Arg Pro Ser Val Pro
                100                 105                 110

Ala His Arg Arg Ala Arg Glu Ser Pro Leu Ser Ser Asp Ala Ile Phe
                115                 120                 125

Lys Gln Ser His Ala Gly Leu Phe Asn Leu Cys Val Val Leu Ile
130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
                180                 185                 190

Phe Thr Val Glu Lys Leu Val Leu Gln Lys Tyr Ile Ser Glu Pro Val
                195                 200                 205

Val Ile Phe Leu His Ile Ile Ile Thr Met Thr Glu Val Leu Tyr Pro
                210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
                260                 265                 270

Asn Pro Glu Val Ser Tyr Tyr Val Ser Leu Lys Ser Leu Ala Tyr Phe
                275                 280                 285

Met Val Ala Pro Thr Leu Cys Tyr Gln Pro Ser Tyr Pro Arg Ser Ala
                290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
                340                 345                 350

Glu Arg Val Leu Lys Leu Ser Val Pro Asn Leu Tyr Val Trp Leu Cys
                355                 360                 365

Met Phe Tyr Cys Phe Phe His Leu Trp Leu Asn Ile Leu Ala Glu Leu
                370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
                420                 425                 430

Thr Leu Ala Ile Ile Ile Ala Phe Leu Val Ser Ala Val Phe His Glu
                435                 440                 445

Leu Cys Ile Ala Val Pro Cys Arg Leu Phe Lys Leu Trp Ala Phe Leu
                450                 455                 460

Gly Ile Met Phe Gln Val Pro Leu Val Phe Ile Thr Asn Tyr Leu Gln
465                 470                 475                 480
```

-continued

```
Glu Arg Phe Gly Ser Thr Val Gly Asn Met Ile Phe Trp Phe Ile Phe
                485             490                 495

Cys Ile Phe Gly Gln Pro Met Cys Val Leu Leu Tyr Tyr His Asp Leu
            500             505                 510

Met Asn Arg Lys Gly Ser Met Ser
        515             520
```